US010456021B2

(12) United States Patent
Shiga et al.

(10) Patent No.: US 10,456,021 B2
(45) Date of Patent: Oct. 29, 2019

(54) ENDOSCOPE APPARATUS AND METHOD FOR OPERATING ENDOSCOPE APPARATUS

(71) Applicant: OLYMPUS CORPORATION, Tokyo (JP)

(72) Inventors: Yuichi Shiga, Hachioji (JP); Toshiaki Mikami, Hachioji (JP); Koichiro Yoshino, Tokyo (JP); Satoshi Takekoshi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/964,383

(22) Filed: Apr. 27, 2018

(65) Prior Publication Data

US 2018/0242828 A1 Aug. 30, 2018

Related U.S. Application Data

(63) Continuation of application No. PCT/JP2015/080726, filed on Oct. 30, 2015.

(51) Int. Cl.
*A61B 1/045* (2006.01)
*A61B 1/00* (2006.01)
(Continued)

(52) U.S. Cl.
CPC .......... *A61B 1/045* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 8,319,870 B2 * 11/2012 Shintani ................... G02B 7/28
  348/294
8,498,529 B2 * 7/2013 Imada .................. G02B 27/646
  348/208.12
(Continued)

FOREIGN PATENT DOCUMENTS

JP H06-197253 A 7/1994
JP H07-234365 A 9/1995
(Continued)

OTHER PUBLICATIONS

International Search Report dated Jan. 19, 2016 issued in PCT/JP2015/080726.

*Primary Examiner* — Clayton E. LaBalle
*Assistant Examiner* — Dennis Hancock
(74) *Attorney, Agent, or Firm* — Scully, Scott, Murphy & Presser, P.C.

(57) ABSTRACT

An endoscope apparatus includes an optical system including a focus lens, a connector to which an interchangeable optical system is connected, an image sensor configured to output a captured image based on the optical system and the interchangeable optical system, and a processor including hardware. The processor performs a determination process of determining whether the interchangeable optical system is a known or unknown optical system, implements a first step amount determination process when the interchangeable optical system is determined to be a known optical system, and implements a second step amount determination process when the interchangeable optical system is determined to be an unknown optical system and controls the focus lens based on step amount information determined.

18 Claims, 15 Drawing Sheets

(51) Int. Cl.

| | |
|---|---|
| *H04N 5/232* | (2006.01) |
| *A61B 1/04* | (2006.01) |
| *H04N 5/235* | (2006.01) |
| *H04N 9/04* | (2006.01) |
| *A61B 1/055* | (2006.01) |
| *H04N 5/225* | (2006.01) |
| *H04N 9/73* | (2006.01) |

(52) U.S. Cl.
CPC ...... *A61B 1/00045* (2013.01); *A61B 1/00059* (2013.01); *A61B 1/00105* (2013.01); *A61B 1/00117* (2013.01); *A61B 1/00126* (2013.01); *A61B 1/00188* (2013.01); *A61B 1/042* (2013.01); *H04N 5/2351* (2013.01); *H04N 5/23212* (2013.01); *H04N 5/23245* (2013.01); *H04N 5/23296* (2013.01); *H04N 5/232123* (2018.08); *H04N 9/045* (2013.01); *A61B 1/055* (2013.01); *H04N 9/735* (2013.01); *H04N 2005/2255* (2013.01)

(56) References Cited

U.S. PATENT DOCUMENTS

| | | | |
|---|---|---|---|
| 8,708,585 B2* | 4/2014 | Osawa | G03B 17/14 |
| | | | 396/529 |
| 9,453,984 B2* | 9/2016 | Hasegawa | G02B 9/00 |
| 2004/0143162 A1* | 7/2004 | Krattiger | A61B 1/00096 |
| | | | 600/175 |

FOREIGN PATENT DOCUMENTS

| | | |
|---|---|---|
| JP | 2005-250127 A | 9/2005 |
| JP | 2010-35131 A | 2/2010 |

* cited by examiner

| SHAPE DATA | KNOWN OR UNKNOWN |
|---|---|
|  | KNOWN |
| ⋮ | ⋮ |

| SIZE OF IMAGE CIRCLE | 300 | 400 | 600 | ... |
|---|---|---|---|---|
| TYPE OF OPTICAL SYSTEM | OPTICAL SYSTEM:A | OPTICAL SYSTEM:D | OPTICAL SYSTEM:E | ... |

| TYPE OF OPTICAL SYSTEM | A | B | ... |
|---|---|---|---|
| STEP AMOUNT REFERENCE VALUE | $(X_{A\_mf}, X_{A\_af})$ | $(X_{B\_mf}, X_{B\_af})$ | ... |

FIG. 16

|  |  | IMAGE CIRCLE SIZE | | |
|---|---|---|---|---|
|  |  | 300 | 400 | ... |
| ZOOM LENS POSITION | WIDE ANGLE END | OPTICAL SYSTEM:A | OPTICAL SYSTEM:D | OPTICAL SYSTEM:E |
|  | 10 | OPTICAL SYSTEM:B | OPTICAL SYSTEM:A | OPTICAL SYSTEM:D |
|  | 20 | OPTICAL SYSTEM:C | OPTICAL SYSTEM:B | OPTICAL SYSTEM:A |
|  | ... | ... | ... | ... |

FIG. 17

|  |  | TYPE OF OPTICAL SYSTEM | | |
|---|---|---|---|---|
|  |  | A | B | ... |
| ZOOM LENS POSITION | WIDE ANGLE END | $(X_{AW\_mf}, X_{AW\_af})$ | $(X_{AW\_mf}, X_{AW\_af})$ | ... |
|  | 10 | $(X_{A10\_mf}, X_{A10\_af})$ | $(X_{B10\_mf}, X_{B10\_af})$ | ... |
|  | 20 | $(X_{A20\_mf}, X_{A20\_af})$ | $(X_{B20\_mf}, X_{B20\_af})$ | ... |
|  | ... | ... | ... | ... |

__US 10,456,021 B2__

ENDOSCOPE APPARATUS AND METHOD FOR OPERATING ENDOSCOPE APPARATUS

CROSS REFERENCE TO RELATED APPLICATION

This application is a continuation of International Patent Application No. PCT/JP2015/080726, having an international filing date of Oct. 30, 2015, which designated the United States, the entirety of which is incorporated herein by reference.

BACKGROUND

Recently used endoscope apparatuses (endoscope systems) use image sensors with a large number of pixels, leading to a shallow depth of field and thus rendering focus adjustment operation for conventional manual focusing (hereinafter, referred to as MF) difficult for users. In view of this, endoscope apparatuses featuring auto focus (hereinafter, referred to as AF) control have been developed.

Lens control (focus lens control) for MF or AF requires lens movement speed or a lens movement amount per unit time (hereinafter, referred to as a step amount) to be appropriately set based on optical characteristics. This is for shortening time required for bringing a subject into focus, and for preventing an unstable operation due to the peak point missed.

Some endoscope apparatuses have a configuration in which a rigid scope serving as an interchangeable optical system is attached to a main body including an image capturing section. Such an interchangeable optical system to be attached can be selected from numerous optical systems.

In JP-A-2005-250127, the shortest possible focusing time is achieved for an AF operation without impairing stability by calculating an appropriate step amount based on an aperture stop status and a zoom lens position obtained by a potentiometer.

In JP-A-2010-35131, a specific lens type is determined based on whether vignetting occurs if the zoom lens position is on the wide angle end side relative to a conversion lens the lens information of which cannot be obtained through an electrical contact and whether the vignetting can be reduced by moving the zoom lens position toward the telephoto end side from the wide angle end side. The settings related to image capturing are changed according to the type determined.

SUMMARY

According to one aspect of the invention, there is provided an endoscope apparatus comprising: an optical system including a focus lens configured to adjust an in-focus object position;
a connector to which an interchangeable optical system is connected;
an image sensor configured to output a captured image based on the optical system and the interchangeable optical system; and
a processor including hardware,
the processor being configured to implement
performing a determination process of determining whether the interchangeable optical system is a known or unknown optical system,
determining step amount information, indicating a control amount of the focus lens of the optical system, based on a first step amount determination process when the interchangeable optical system is determined to be a known optical system, or based on a second step amount determination process, different from the first step amount determination process, when the interchangeable optical system is determined to be an unknown optical system, and
controlling the focus lens based on the step amount information determined.

According to another aspect of the invention, there is provided a method for operating an endoscope apparatus including an optical system including a focus lens configured to adjust an in-focus object position and a connector to which an interchangeable optical system is connected, the method comprising:
performing a determination process of determining whether the interchangeable optical system is a known or unknown optical system;
determining step amount information, indicating a control amount of the focus lens of the optical system, based on a first step amount determination process when the interchangeable optical system is determined to be a known optical system or based on a second step amount determination process, different from the first step amount determination process, when the interchangeable optical system is determined to be an unknown optical system; and
controlling the focus lens based on the step amount information determined.

BRIEF DESCRIPTION OF THE DRAWINGS

FIG. 16 is a table illustrating another configuration example of data used for an identification process of the type of the interchangeable optical system.

FIG. 17 is a table illustrating another configuration example of data used for determination of step amount information based on the type of the interchangeable optical system.

DESCRIPTION OF EXEMPLARY EMBODIMENTS

Figure 1A:
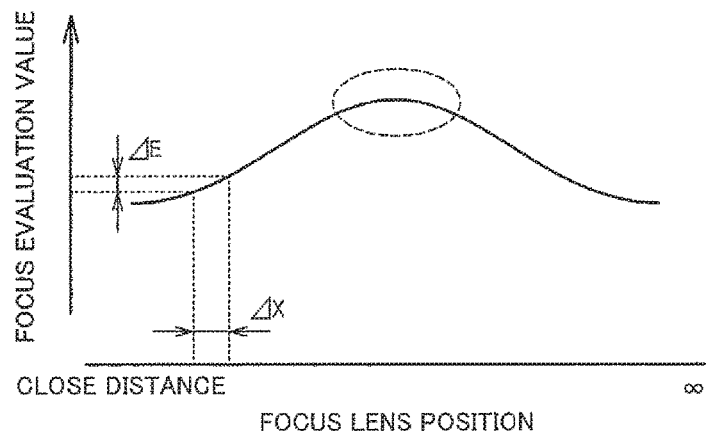
FIG. 1A and FIG. 1B are charts illustrating relationship between a focus lens position and a focus evaluation value changing in accordance with optical characteristics.

According to one embodiment of the invention, there is provided an endoscope apparatus comprising: an optical system including a focus lens configured to adjust an in-focus object position;

a connector to which an interchangeable optical system is connected;

an image sensor configured to output a captured image based on the optical system and the interchangeable optical system; and a processor including hardware, the processor being configured to implement performing a determination process of determining whether the interchangeable optical system is a known or unknown optical system, determining step amount information, indicating a control amount of the focus lens of the optical system, based on a first step amount determination process when the interchangeable optical system is determined to be a known optical system, or based on a second step amount determination process, different from the first step amount determination process, when the interchangeable optical system is determined to be an unknown optical system, and controlling the focus lens based on the step amount information determined.

According to another embodiment of the invention, there is provided a method for operating an endoscope apparatus including an optical system including a focus lens configured to adjust an in-focus object position and a connector to which an interchangeable optical system is connected, the method comprising:

performing a determination process of determining whether the interchangeable optical system is a known or unknown optical system;

determining step amount information, indicating a control amount of the focus lens of the optical system, based on a first step amount determination process when the interchangeable optical system is determined to be a known optical system or based on a second step amount determination process, different from the first step amount determination process, when the interchangeable optical system is determined to be an unknown optical system; and controlling the focus lens based on the step amount information determined.

The present embodiment will be described below. The present embodiment described below does not unduly limit the scope of the present invention described in the appended claims. Note also that not all of the elements described below in connection with the exemplary embodiments should be taken as essential elements of the invention.

1. Method According to Present Embodiment

First of all, a method according to the present embodiment is described. As disclosed in JP-A-2005-250127, how a focus evaluation value changes due to a change in the position of a focus lens depends on the characteristics of an optical system. The focus evaluation value is information indicating focusing degree of a subject of image capturing (in particular, a subject in an area, in a captured image, to be a target of focus evaluation value calculation). For example, the focus evaluation value may be various types of information such as a contrast value in contrast AF.

Figure 1B:
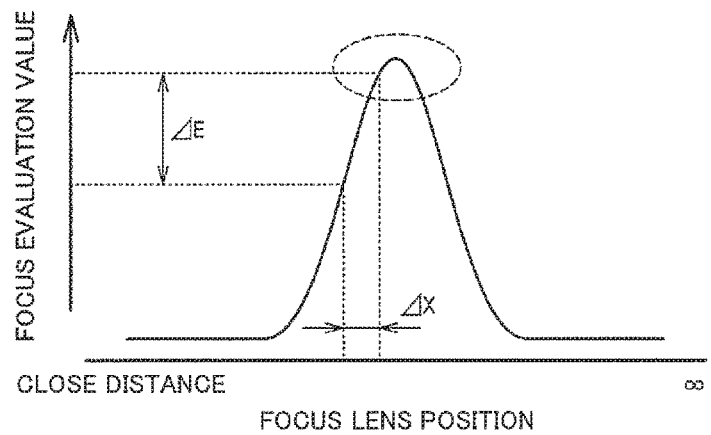

FIG. 1A and FIG. 1B illustrate specific examples of a focus lens position and a focus evaluation value. In FIG. 1A and FIG. 1B, the horizontal axis represents the focus lens position. A left side and a right side of the axis respectively represent a near point side, with an in-focus object position being close to an image sensor, and a far point side. The in-focus object position as used herein represents a position of an object when a system, including an optical system, an image plane (a plane of an image sensor in a narrow sense), and an object (subject), is in an in-focus state. The vertical axis in the figures represents the focus evaluation value.

FIG. 1A illustrates a case where a rate of change of the focus evaluation value relative to a change in the focus lens position is small. In other words, an amount of change $\Delta E$ of the focus evaluation value involved in a movement of the focus lens position by $\Delta x$ is relatively small, for example. FIG. 1B illustrates a case where the rate of change of the focus evaluation value relative to a change in the focus lens position is large, with the amount of change $\Delta E$ in the focus evaluation value, involved in the movement of the focus lens position by $\Delta x$, being larger than that in FIG. 1A.

The focus evaluation value reaches the peak (the maximum value in the examples of the focus evaluation value in FIG. 1A and FIG. 1B) when the subject is in focus. Thus, focus control needs the movement of the focus lens to a position with such a peak value or to a position sufficiently close to such a peak position.

As described in JP-A-2005-250127, a control amount of the focus lens position set without taking fluctuation in characteristics, as illustrated in FIG. 1A and FIG. 1B, into consideration might result in unfavorable conditions. For example, relatively large $\Delta x$ set in the case illustrated in FIG. 1B might result in a failure to appropriately detect the peak, or might even result in an unstable behavior with the focus lens position fluctuating around the peak position without stabilizing. Thus, in the case illustrated in FIG. 1B, $\Delta x$ needs to be set to be small enough not to miss the peak.

If $\Delta x$, which is as large as that in FIG. 1B, is set for the case illustrated in FIG. 1A, where the amount of change $\Delta E$ of the focus evaluation value is small, a long period of time is required for bringing the subject into focus. If a change in the focus evaluation value is small, a method of determining an in-focus direction with the focus lens moved back and forth from a reference position (what is known as wobbling) might result in a failure to appropriately determine the direction. Thus, $\Delta x$ should be set to be larger in the case illustrated in FIG. 1A than in the case illustrated in FIG. 1B. JP-A-2005-250127 discloses a method of calculating the movement amount and speed of a focus lens, corresponding to $\Delta x$, based on optical characteristics.

The method disclosed in JP-A-2005-250127 relies on information, representing the optical characteristics detected by a potentiometer (representing a zoom lens position and an aperture stop status), acquired via an electrical contact provided to a connection section between an optical system and a camera main body. Thus, the method disclosed in JP-A-2005-250127 cannot be implemented in a situation where the information on the optical characteristics of the optical system cannot be acquired from the optical system.

In view of this, JP-A-2010-35131 discloses a method of determining whether a conversion lens connected is a telephoto conversion lens or a wide angle conversion lens, based on an image circle size. The method disclosed in JP-A-2010-35131 enables the type of the conversion lens to be determined even when the information on the optical characteristics of the conversion lens cannot be directly acquired (via the electrical contact). However, the method disclosed in JP-A-2010-35131 is for merely determining whether the optical system attached is a telephoto conversion lens or a wide angle conversion lens, and is not usable for more detailed determination including identifying a specific type of the optical system. Thus, the method disclosed in JP-A-2010-35131 covers only known optical systems to be attached, and is not applicable to cases where unknown optical systems are connected.

Figure 2:
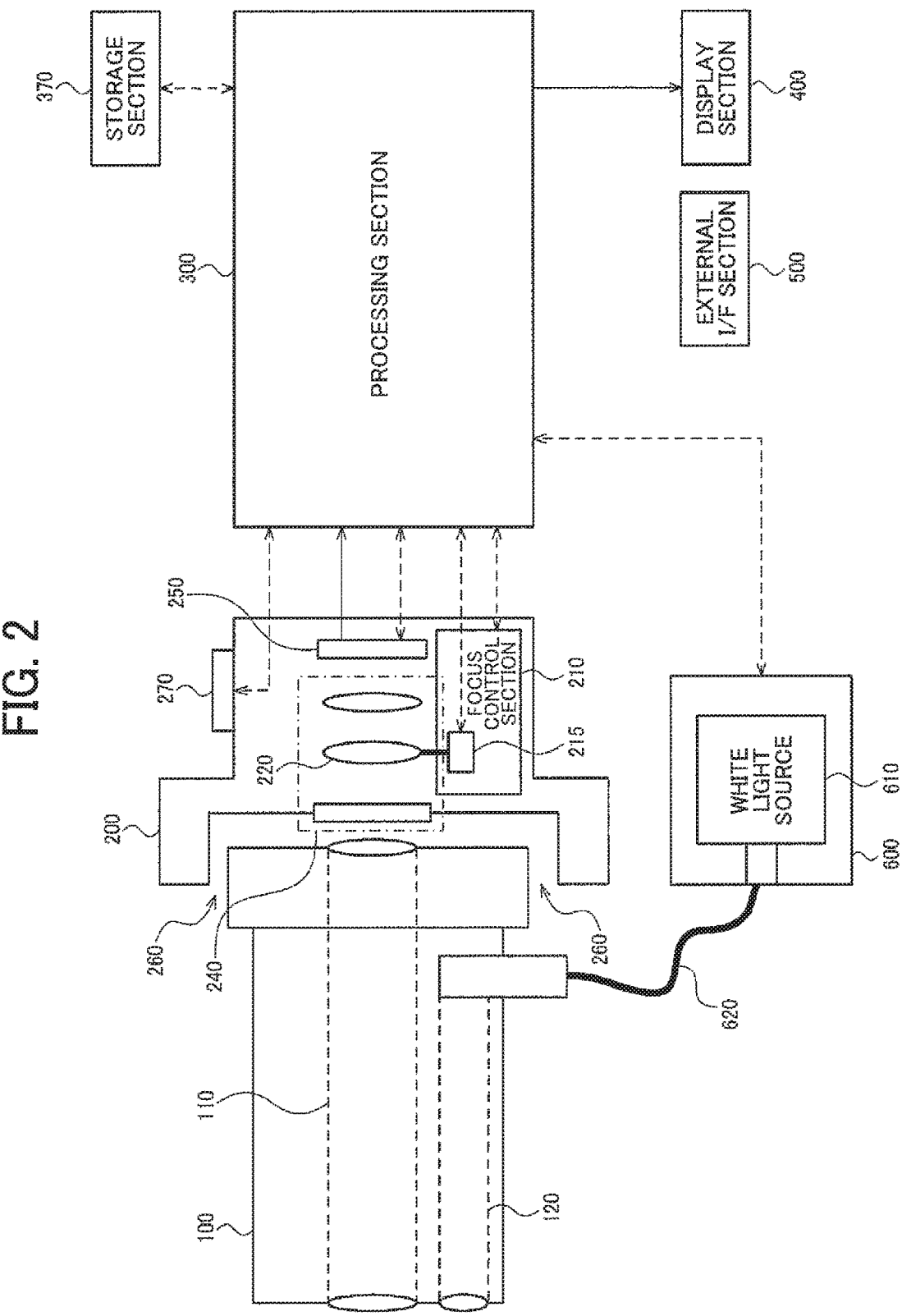
FIG. 2 is a diagram illustrating a system configuration example of an endoscope apparatus.

An endoscope apparatus according to the present embodiment, in particular, an endoscope apparatus for surgery has an interchangeable optical system 100 connected to a connection section 260 (a connection section for a camera head, for example) as illustrated in FIG. 2. This interchangeable optical system 100 is a rigid scope inserted into an examination target. Another optical system 240 is provided in the endoscope apparatus (in the camera head), and a subject image formed with the optical system 240 and the interchangeable optical system 100 is acquired as a captured image. The shape of the graphs as illustrated in FIG. 1A and FIG. 1B changes in accordance with the optical characteristics of the optical system 240 and the interchangeable optical system 100. Thus, the focus lens control, for the endoscope apparatus with the interchangeable optical system 100 attached, needs to be adjusted in accordance with the interchangeable optical system 100 attached.

The rigid scope serving as the interchangeable optical system 100 is a member inserted into the examination target, specifically a patient, and thus is subjected to treatments such as sterilization and disinfection. Thus, the electrical contact provided to a rigid scope could be a failure factor in the rigid scope. In view of this, rigid scopes are typically provided with no electrical contact.

Various types of rigid scopes are selected to be used for various surgery target portions (organs), surgical details, and the like. The rigid scopes typically have no electrical contact as described above, and thus are less likely to be limited by particular attachable interchangeable optical systems, as in the case of digital cameras with a mount. For example, a digital camera is limited by particular attachable lenses in accordance with the type (the manufacturer or model) of a main body of the digital camera. However, the endoscope apparatus, which is a subject matter of the present embodiment, is supposed to enable various types of rigid scopes to be attached (a rigid scope manufactured by a manufacturer different from that of the main body, for example).

Thus, the present invention is directed to a situation where the information is difficult to directly acquire via the electrical contact or the like and needs to enable unknown interchangeable optical systems to be attached. The methods disclosed in JP-A-2005-250127 and JP-A-2010-35131 are difficult to achieve appropriate focus control in such a situation.

Thus, the present applicant proposes a method of achieving appropriate focus control even in such a situation. Specifically, as illustrated in FIG. 2, the endoscope apparatus according to the present embodiment includes an optical system 240 including a focus lens 220 configured to adjust an in-focus object position, a connection section 260 to which the interchangeable optical system 100 is connected, an image sensor 250 configured to output a captured image based on the optical system 240 and the interchangeable optical system 100, a focus control section 210 configured to control the focus lens 220 based on step amount information representing a control amount of the focus lens 220 in the optical system 240, and a processing section 300. The processing section 300 performs a determination process of determining whether the interchangeable optical system 100 is a known or unknown optical system. As a result, when the interchangeable optical system 100 is determined to be a known optical system, the step amount information is determined based on a first step amount determination process. When the interchangeable optical system 100 is determined to be an unknown optical system, the step amount information is determined based on a second step amount determination process different from the first step amount determination process. The step amount information thus determined is output to the focus control section 210.

Figure 3A:
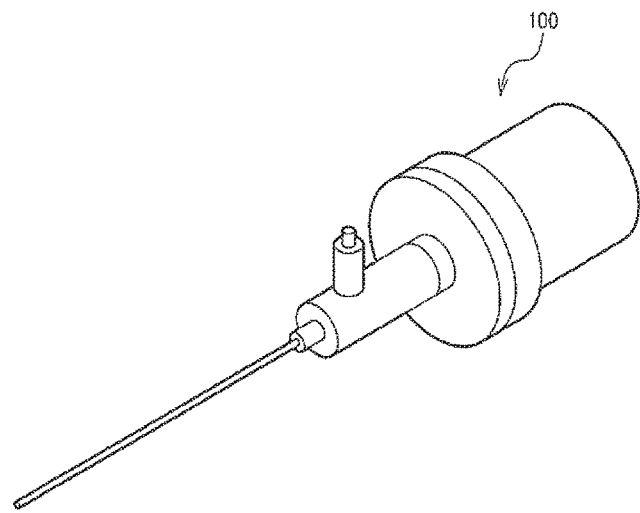
FIG. 3A and FIG. 3B are outer views of an interchangeable optical system.
Figure 3B:
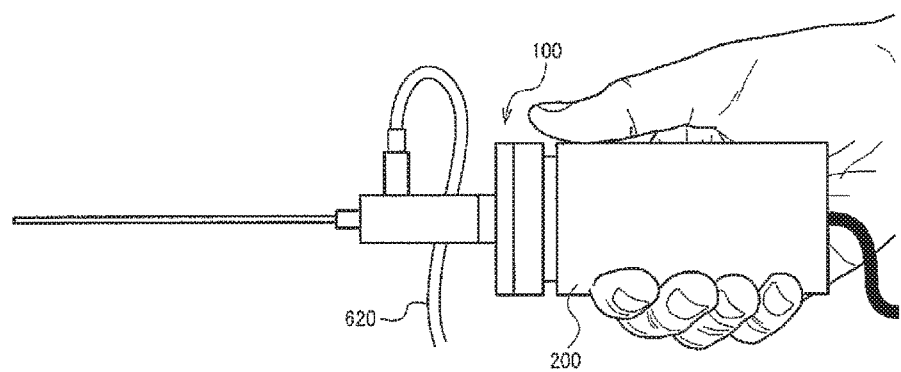

The interchangeable optical system 100 is a rigid scope, in a narrow sense, including an inserted section to be inserted into a patient body as illustrated in FIG. 3A and FIG. 3B. FIG. 3A is an outer view of the interchangeable optical system 100 that is a rigid scope. FIG. 3B is a diagram illustrating a state where the rigid scope is connected to the endoscope apparatus (an image capturing section 200 or a camera head in a narrow sense) via the connection section 260.

The step amount information is information, corresponding to Δx in FIG. 1A and FIG. 1B, representing a position, a movement amount, and a movement speed of the focus lens.

Figure 4:
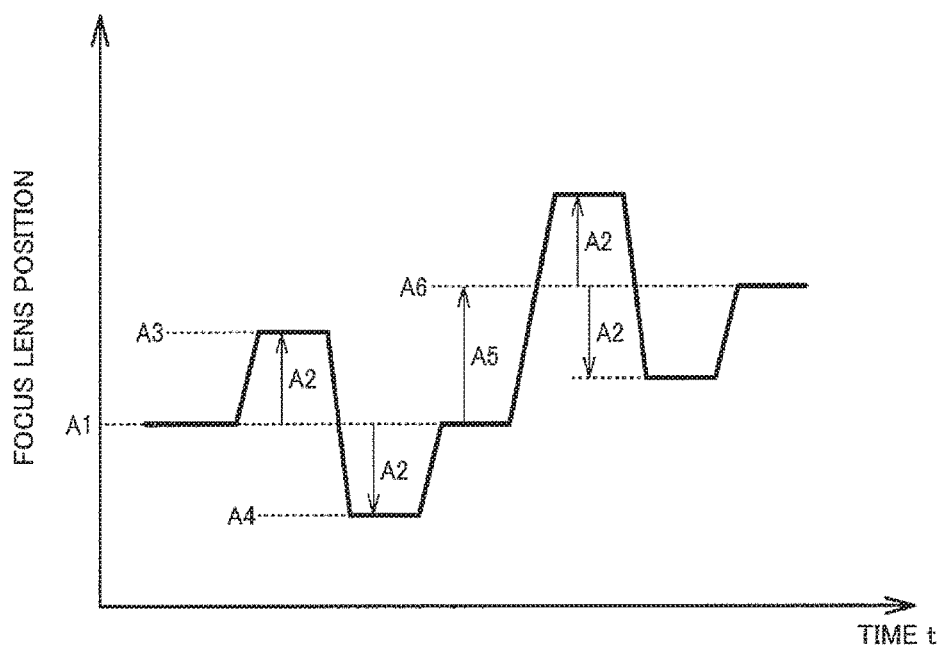
FIG. 4 is a chart illustrating step amount information based on wobbling.

For example, when an AF operation is based on wobbling, the step amount information may be one of a wobbling amount and an amount of movement of the focus lens as a result of a single direction determination or both. FIG. 4 illustrates an example of the focus lens control based on wobbling. In the figure, the horizontal axis represents time and the vertical axis represents the focus lens position. The wobbling is performed with the focus lens moved by a wobbling amount (A2) from the current focus lens position serving as a reference position (A1) to obtain focus evaluation values. In the example illustrated in FIG. 4, the focus lens is moved toward both a far point side (A3) and a near point side (A4) relative to A1. Then, focus evaluation values obtained at A3 and A4 are compared with each other, and the reference position of the focus lens is changed to be on a side on which a larger one of the focus evaluation values is obtained. In the example illustrated in FIG. 4, the focus evaluation value obtained at A3 is larger than that obtained at A4, and thus the focus lens is moved toward the far point side by a predetermined amount (A5), and thus the reference position is newly set to be at A6. The step amount information, serving as the amount of change A5 of the reference position, may be changed based on the interchangeable optical system 100 to prevent the peak from being missed in the case illustrated in FIG. 1B and shorten the time required for bringing the subject into focus in the case illustrated in FIG. 1A. The step amount information, which is the wobbling amount (A2), may be changed in accordance with the interchangeable optical system 100 to appropriately determine a moving direction of the reference position (a direction of a slope in the graph) in the case illustrated in FIG. 1A.

The AF operation is not limited to such an operation based on wobbling, and may be performed by calculating (scanning) the focus evaluation values, while changing the focus lens position within a certain range to obtain the peak. For example, the focus evaluation values may be obtained at P focus lens positions, and the peak may be detected through approximation using a given function. In this configuration, the number of positions for obtaining the focus evaluation values is preferably small in the case illustrated in FIG. 1A and is preferably large in the case illustrated in FIG. 1B. Thus, the step amount information used in this configuration is information representing a value of P or an interval of the points. Thus, the step amount information represents the focus lens position and a movement amount of the focus lens from a given focus lens position to the next focus lens position.

The focus control according to the present embodiment may be performed by an MF operation. The MF operation is an operation of controlling the focus lens position in accordance with a user operation (an operation of pressing a focus button or an operation of rotating a focus dial, for example). In this configuration, the focus lens should move largely or quickly based on the user operation in the case illustrated in FIG. 1A, and should not move largely or should move slowly in the case illustrated in FIG. 1B. Thus, the step amount information is information to achieve control the movement in this manner. For example, the step amount information may be information representing a movement amount of the focus lens per unit user operation (such as an operation of pressing the button once or rotating the dial by a predetermined amount). Alternatively, the movement speed may be changed with the movement amount of the focus lens per unit user operation fixed. For example, in the case illustrated in FIG. 1A, the focus lens position quickly responds to the user operation. In the case illustrated in FIG. 1B, the focus lens position may take a long time for the movement to finally arrive at the same focus lens position (respond slowly). Thus, the step amount information may be a response (movement speed) of the focus lens.

Control information corresponding to the actual step amount information also varies depending on the configuration of a driving section (an optical system driving section 215 described below, serving as an actuator in a narrow sense) that drives the focus lens. The driving section may be a stepping motor. In such a case, the movement amount of the focus lens is controlled based on a driving amount, that is, the number of steps. Thus, the step amount information is information designating the number of steps. The driving section may be a voice coil motor (VCM). In such a case, the focus lens position is directly controlled. Thus, the movement speed is controlled with a timing of moving to each position or the like controlled. All things considered, the step amount information is information with which a timing and a target position of the movement of the focus lens can be designated to the VCM.

There are various specific examples of the step amount information as described above. Note that the step amount information of any of the specific examples is for controlling at least one of the position, the movement amount, and the movement speed of the focus lens. The step amount information is denoted with a sign X or the like, and the content thereof will not be described in detail. Note that the step amount information may be any one of the types of information described above, or may be any other type of information similar to those described above. As will be described later, the step amount information is set through a procedure including: determining a step amount reference value; and then setting a specific value (hereinafter, referred to as a step amount) based on the step amount reference value. The step amount information according to the present embodiment includes both of the step amount reference value and the step amount obtained based on the step amount reference value.

As is apparent from FIG. 1A and FIG. 1B, even when the optical characteristics are uniquely determined, the inclination of the graph is small in a skirt portion (a portion far from the peak position) of a mountain shape defined with the graph, and is large in a portion at the top (a portion near the peak position). Thus, the step amount needs to be different between the cases illustrated in FIG. 1A and FIG. 1B, and is preferably changed in accordance with the focus lens position in the case illustrated in each of FIG. 1A and FIG. 1B. Thus, in the present embodiment, the step amount reference value serving as a reference of the step amount determined in accordance with the interchangeable optical system 100, with the actual step amount determined with reference to another type of information such as the focus lens position. The description below is based on an assumption that a first step amount reference value determination section 350 and a second step amount reference value determination section 360 determine the step amount reference value, and a step amount control section 211 outputs a step amount (or a corresponding control signal) based on the step amount reference value.

The method according to the present embodiment includes determining whether the interchangeable optical system 100 is a known optical system and switching a step amount information determination process based on a result of the determination. The step amount information is determined using a feature amount of a captured image. Thus, appropriate focus control can be performed even when the optical characteristics of the interchangeable optical system cannot be directly acquired using a sensor or the like. For an unknown optical system, a step amount determination process different from that for a known optical system can be performed, whereby appropriate control can be performed with any of a wide variety of interchangeable optical systems attached.

The processing section 300 may perform a first step amount determination process, when the interchangeable optical system 100 attached is determined to be a known optical system, for determining the step amount information based on the type of the interchangeable optical system identified.

Thus, the step amount information can be determined in accordance with a result of identifying the specific type of the interchangeable optical system 100 attached, instead of merely determining whether the optical system attached is a telephote conversion lens or a wide angle conversion lens as in JP-A-2010-35131. For example, a specific example of this process, which may be performed with reference to a lookup table (LUT), is described later with reference to FIG. 11, FIG. 12, and the like.

The first step amount determination process is assumed to include two processes including: a process of identifying the type of the interchangeable optical system; and a process of determining the step amount information based on the type thus identified. In an example illustrated in FIG. 5 to FIG. 7 described later, a first step amount information determination process is implemented with an identification process performed by an interchangeable optical system determination section 340 and a step amount reference value determination process performed by the first step amount reference value determination section 350. Note that the known/unknown determination process and the type identification process may both be performed using a feature amount obtained from a captured image, with a matching process using a single piece of table data as in a modification of a first embodiment described later with reference to FIG. 14. In such a case, a part (identification process) of the determination process and the first step amount information determination process is implemented with the matching process.

The processing section 300 may perform a second step amount determination process of setting the step amount information to be a given setting value when the interchangeable optical system 100 attached is determined to be an unknown optical system.

Thus, focus control using optimum step amount information can be performed for a known optical system, and focus control with a lower risk of problems using highly versatile step amount information can be performed for an unknown optical system. The given setting value can be set based on various aspects. For example, the endoscope apparatus according to the present embodiment is supposed to be used for medical purposes, and thus needs to be prevented from behaving unstably. Thus, step amount information to achieve a relatively small movement amount or a relatively low movement speed may be used, as in the case illustrated in FIG. 1B, so that the peak will not be missed and the focus lens position can be prevented from being unstable. Such information might fail to correctly determine the direction in wobbling when the actually attached optical system has the optical characteristics as illustrated in FIG. 1A. Thus, in such a case, the focus control may be performed based on the MF, with the AF disabled as described later. Alternatively, an intermediate value may be set to ensure a certain level of accuracy in both of the cases illustrated in FIG. 1A and FIG. 1B. Furthermore, the setting value may be set in accordance with another type of information such as a result of determining an observation target such as an organ through image processing, user input, or the like, for example. Thus, various setting values may be used for the second step amount determination process.

The endoscope apparatus according to the present embodiment includes a memory (storage section 370) that stores information (such as a program and various types of data for example) and a processor (the processing section 300, a processor including hardware) that operates based on the information stored in the memory. The processor performs a process of determining whether the interchangeable optical system 100 is a known or unknown optical system, determines the step amount information based on the first step amount determination process when the interchangeable optical system 100 is determined to be a known optical system, determines the step amount information based on the second step amount determination process different from the first step amount determination process when the interchangeable optical system 100 is determined to be an unknown optical system, and outputs the step amount information thus determined to the focus control section 210.

For example, the function of each section of the processor (processing section 300) may be implemented by individual pieces of hardware or may be implemented by integrated hardware. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application specific integrated circuit (ASIC). The memory (storage section 370) may be a semiconductor memory (e.g., SRAM or DRAM), or may be a register. The memory (storage section 370) may be a magnetic storage device such as a hard disk drive (HDD), or may be an optical storage device such as an optical disc device. For example, the memory stores a computer-readable instruction, and the function of each section of the processing section 300 is implemented by causing the processor to perform the instruction. The instruction may be an instruction set that is included in a program, or may be an instruction that instructs the hardware circuit included in the processor to operate.

For example, an operation of the present embodiment is implemented as follows. The image capturing section 200 captures an image, and this captured image (image data) is processed by the processing section 300 (processor) and is stored in the storage section 370 (memory). The interchangeable optical system determination section 340 (which will be described in detail later with reference with FIG. 5, and the same applies to the sections of the processing section 300) performs a process of determining whether the interchangeable optical system 100 is a known or unknown optical system, and stores a result of the determination in the storage section 370. The determination process may be performed using a feature amount calculated from a captured image as described later in first and second embodiments. In this configuration, the processing section 300 performs preprocess including: reading the captured image from the storage section 370, performing a feature amount calculation process; and storing the feature amount thus calculated in the storage section 370. Under this condition, the processing section 300 reads the feature amount from the storage section 370, reads information (data in FIG. 9 for example) for the determination process from the storage section 370, performs a comparison process (matching process), and writes a result of the process to the storage section 370. When the interchangeable optical system 100 is a known optical system, the interchangeable optical system determination section 340 identifies the type of the interchangeable optical system 100, and stores a result of the identification in the storage section 370.

A control section 320 reads a result of the determination (a known or an unknown optical system) from the storage section 370, and operates any one of the first step amount reference value determination section 350 and the second step amount reference value determination section 360 based on the result of the determination thus read. The first step amount reference value determination section 350 operates when the result of the determination, read from the storage section 370, is a known optical system, to read a result of identifying the type of the interchangeable optical system 100 from the storage section 370 and determine the step amount reference value by using the identification result and table data (data in FIG. 12 for example) stored in the storage section 370. The second step amount reference value determination section 360 operates when the result of the determination, read from the storage section 370, is an unknown optical system, to determine the step amount reference value based on a given setting value stored in the storage section 370.

The focus control section 210 operates based on the control information from the processing section 300 (control section 320) to control the optical system 240 including the focus lens 220. A part (the step amount control section 211 for example) of the focus control section 210 may be implemented with the processor. In such a case, the processor (step amount control section 211) determines the step amount to be output to the optical system control section 213, based on the step amount reference value and another type of control information (information indicating the focus lens position and the aperture stop status, for example). The storage section 370 may store information used for the determination (such as a function using the step amount reference value and the control information as inputs and the step amount as outputs or a LUT, for example), and the processor may read the information from the storage section 370 to output the step amount. The focus control section 210 may be operable under the MF mode and the AF mode. In such a case, the processor may write and read mode control information (mode flag) to and from the storage section 370 to perform mode control.

2. First Embodiment

A first embodiment is described below. Specifically, a system configuration example of an endoscope apparatus is described, followed by a detailed process. Then, the modification of the first embodiment is described.

2.1 System Configuration Example

FIG. 2 mentioned above is a block diagram illustrating an overall configuration of the endoscope apparatus according to the present embodiment. As illustrated in FIG. 2, the endoscope apparatus includes the image capturing section 200 (camera head), the processing section 300, the storage section 370, a display section 400, an external OF section 500, and a light source section 600. The image capturing section 200 includes the connection section 260, the optical system 240, the image sensor 250, and the focus control section 210. The interchangeable optical system 100 is connected to the image capturing section 200.

Figure 5:
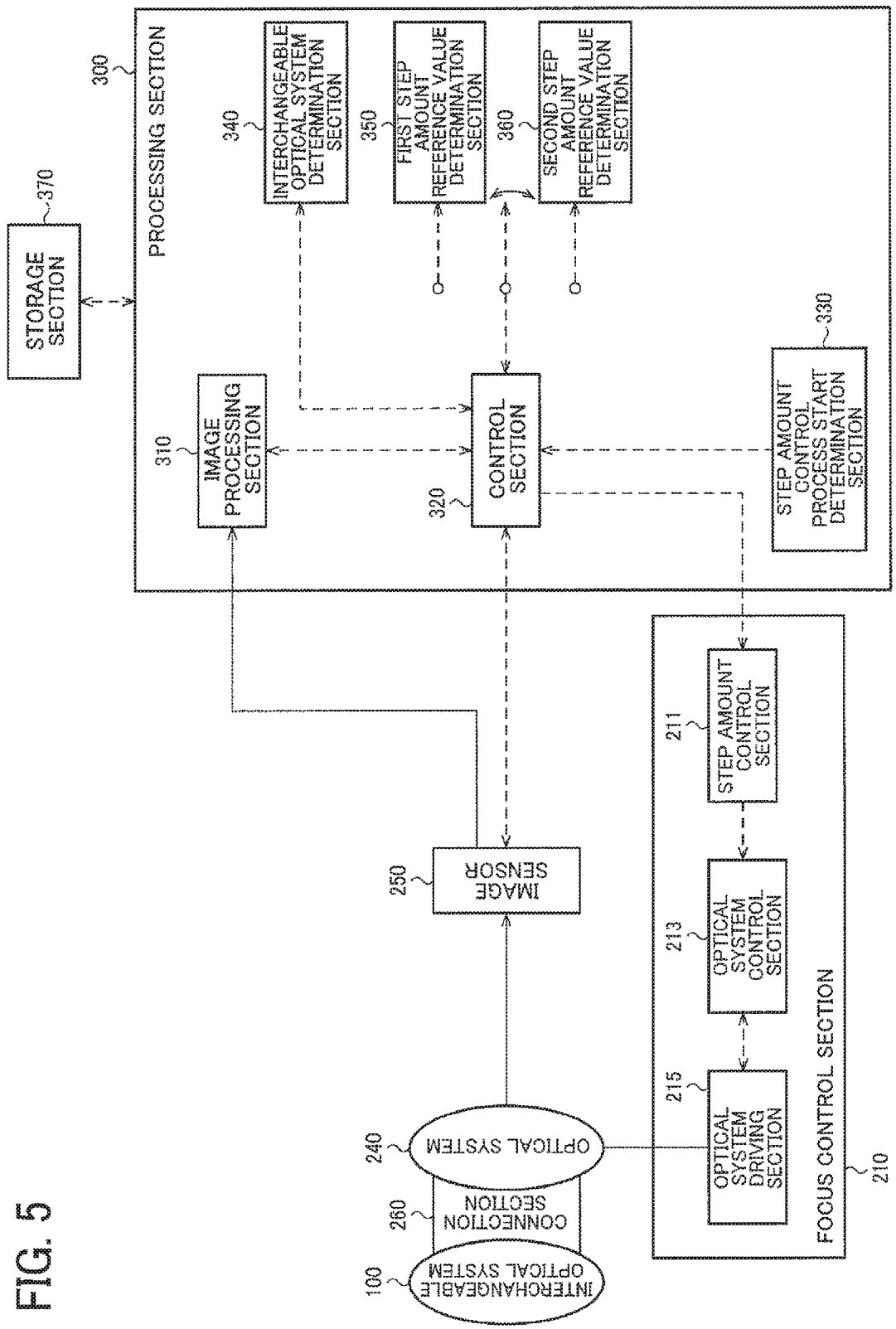
FIG. 5 is a diagram illustrating a system configuration example of the endoscope apparatus.

FIG. 5 is a diagram illustrating a configuration example of the focus control section 210 and the processing section 300. As illustrated in FIG. 5, the focus control section 210 includes the step amount control section 211, the optical system control section 213, and the optical system driving section 215. The processing section 300 includes an image processing section 310, the control section 320, a step amount control process start determination section 330, the interchangeable optical system determination section 340, the first step amount reference value determination section 350, and the second step amount reference value determination section 360.

Note that the endoscope apparatus is not limited to the configurations illustrated in FIG. 2 and FIG. 5, and various modifications including omitting some of these components and adding other components may be made. For example, in FIG. 2, the focus control section 210 includes the step amount control section 211 and the optical system control section 213. However, this should not be construed in a limiting sense, and the processing section 300 may include the step amount control section 211 and the optical system control section 213. In FIG. 2, the image capturing section 200 and the processing section 300 are illustrated as different hardware configurations. For example, the image capturing section 200 is implemented as a camera head, and the processing section 300 is implemented as a processing device connected to the camera head through a cable or the like. This configuration can be modified. For example, the camera head may have functions of the processing device, and the image capturing section 200 may include both of the focus control section 210 and the processing section 300. Alternatively, functional blocks of the processing section 300 may be partially provided in the image capturing section 200.

The endoscope apparatus according to the present embodiment is an endoscope apparatus, used for laparoscopic surgery for example, to which a rigid scope (interchangeable optical system 100) can be detachably attached. The detachably attached interchangeable optical system 100 can be connected and secured to the optical system 240 via the connection section 260. As described above, the connection section 260 might have no electrical contact. The interchangeable optical system 100 may include a light guide section 120 that guides light, emitted from the light source section 600 illustrated in FIG. 2, to an end of the interchangeable optical system 100. For example, the light source section 600 includes a white light source 610 that emits white light and a light guide cable 620 that guides the light, emitted from the white light source, to the interchangeable optical system 100. The light guide section 120 of the interchangeable optical system 100 may guide the light, emitted from the light guide cable 620, to the end. For example, an actual optical system (lens system 110) in the interchangeable optical system 100 includes an object lens, a relay lens, and an eyepiece.

The optical system 240 can be controlled by the focus control section 210 and at least includes the focus lens 220. As will be described later in the second embodiment, the optical system 240 may include a zoom lens 230, and the optical system driving section 215 may drive the focus lens 220 and the zoom lens 230.

The image sensor 250 acquires a subject image formed with the two optical systems including the interchangeable optical system 100 and the optical system 240 to generate a captured image, and transmits the image data thus obtained to the image processing section 310. The image sensor 250 is a primary color Bayer image sensor in which any of R, G, and B color filters is disposed in a Bayer array, for example. Alternatively, an image sensor that utilizes a complementary color filter, a stacked image sensor that is designed so that each pixel can receive light having a different wavelength without using a color filter, and a monochrome image sensor that does not utilize a color filter may be employed as long as the subject can be captured to obtain an image.

The image processing section 310 performs various types of processing on the captured image. For example, the image processing section 310 performs image processing including a white balance process and an interpolation process (demosaicing process). The process of calculating the feature amount of the captured image is assumed to be performed by the interchangeable optical system determination section 340. However, a modification where the image processing section 310 is in charge of the process may be employed.

The control section 320 is connected to various sections of the endoscope apparatus, and controls the sections. Specifically, the control section 320 performs control to determine which one of the first step amount reference value determination section 350 and the second step amount reference value determination section 360 is to be operated based on a result of the determination by the interchangeable optical system determination section 340, control to output the set step amount reference value to the focus control section 210 (the step amount control section 211 in a narrow sense), and the other like control.

The step amount control process start determination section 330 determines whether or not to start a series of processes to determine the step amount information. The interchangeable optical system determination section 340 determines whether the interchangeable optical system 100 attached is a known or unknown optical system, and determines (identifies) the specific type if the known optical system is attached. The first step amount reference value determination section 350 performs the first step amount information determination process (the type identification process may be performed by the interchangeable optical system determination section 340 as described above). The second step amount reference value determination section 360 performs the second step amount information determination process. The first step amount reference value determination section 350 and the second step amount reference value determination section 360 determine and output the step amount reference value to be a reference for calculating a specific step amount.

The storage section 370 serves as a work area for the processing section 300, and has functions that can be implemented with a memory such as a random access memory (RAM) and a hard disk drive (HDD). For example, the storage section 370 stores information including: information used for the determination process by the interchangeable optical system determination section 340; and information used for determining the step amount information (step amount reference value) by the first step amount reference value determination section 350 or the second step amount reference value determination section 360. An example of a specific data format is described later with reference to FIG. 11, FIG. 12, and the like.

The step amount control section 211 generates a control signal corresponding to the step amount, based on a command transmitted from the control section 320 and the step amount reference value and transmits the signal to the optical system control section 213. The optical system control section 213 generates a drive signal based on the control signal, and transmits the drive signal to the optical system driving section 215. The optical system driving section 215 drives the optical system 240 (the focus lens 220 thereof in a narrow sense) in an optical axis direction based on the drive signal. The optical system driving section 215 may be implemented with various actuators including a stepping motor, a VCM, or the like as described above.

The display section 400 is a liquid crystal monitor for example, and displays images sequentially output from the processing section 300.

2.2 Detail of Process

Figure 6:
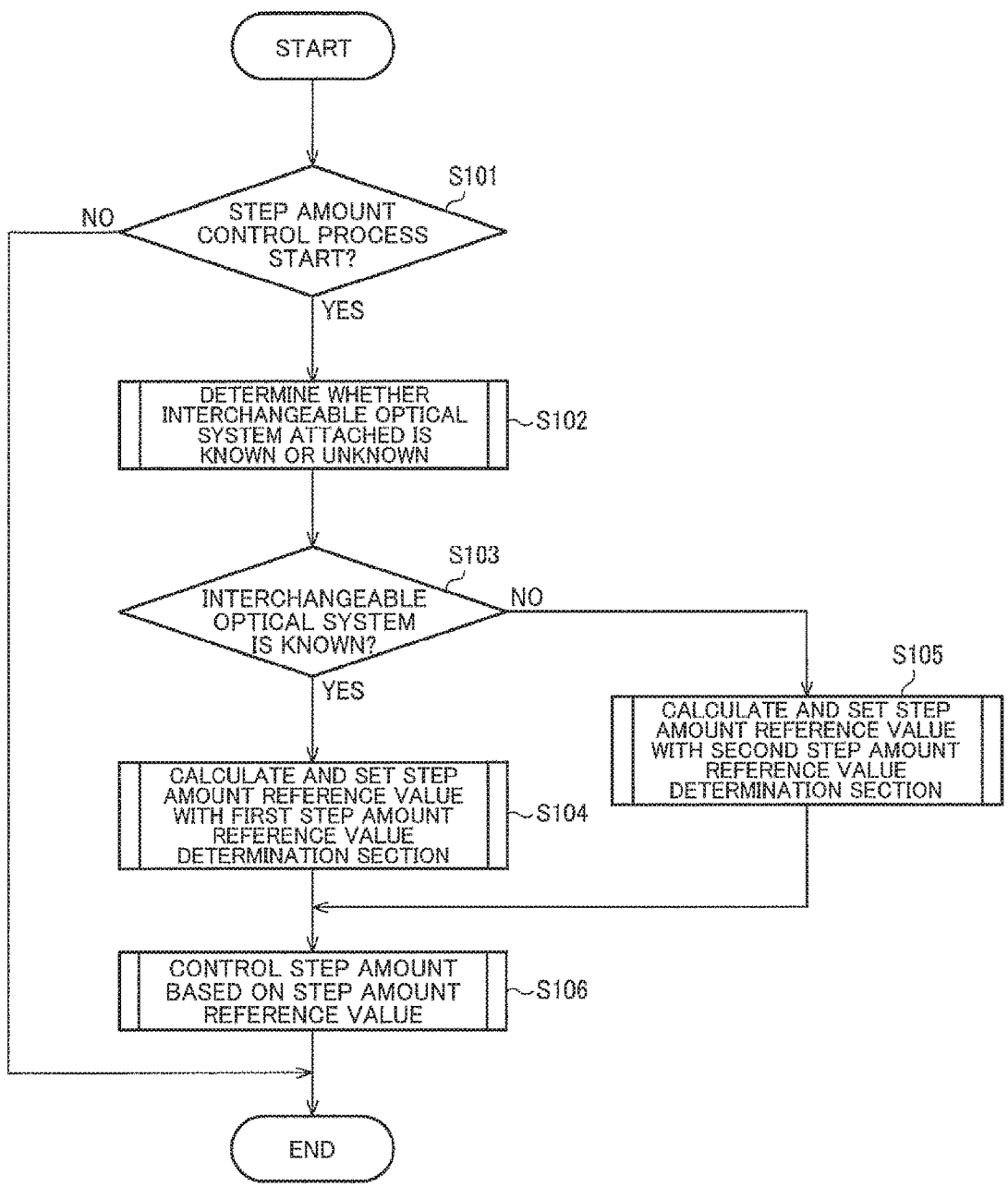
FIG. 6 is a flowchart illustrating a process according to the present embodiment.

The process of setting the step amount is described in detail below with reference to a flowchart in FIG. 6. First of all, the step amount control process start determination section 330 determines whether or not to start the step amount control process (S101). For example, when an instruction to start white balance adjustment is issued to the endoscope apparatus from the outside, a signal indicating such an instruction is provided to the step amount control process start determination section 330, and triggers the step amount control process start determination section 330 to output a step amount control process start signal to the control section 320.

The control section 320 starts the determination process for the interchangeable optical system 100, upon receiving the process start signal from the step amount control process start determination section 330. The control section 320 issues a start command to the interchangeable optical system determination section 340, to determine whether the interchangeable optical system 100 attached is a known or unknown optical system, and acquires information indicating the type of the optical system if the known optical system is attached (S102).

Specifically, the process in S102 is performed by the interchangeable optical system determination section 340. The interchangeable optical system determination section 340 uses an image output from the image processing section 310 to perform the determination on the interchangeable optical system 100 attached, and outputs a result of the determination (a known or unknown optical system), as well as a result of identifying the type of the interchangeable optical system 100 if the known optical system is attached, to the control section 320.

Figure 7:
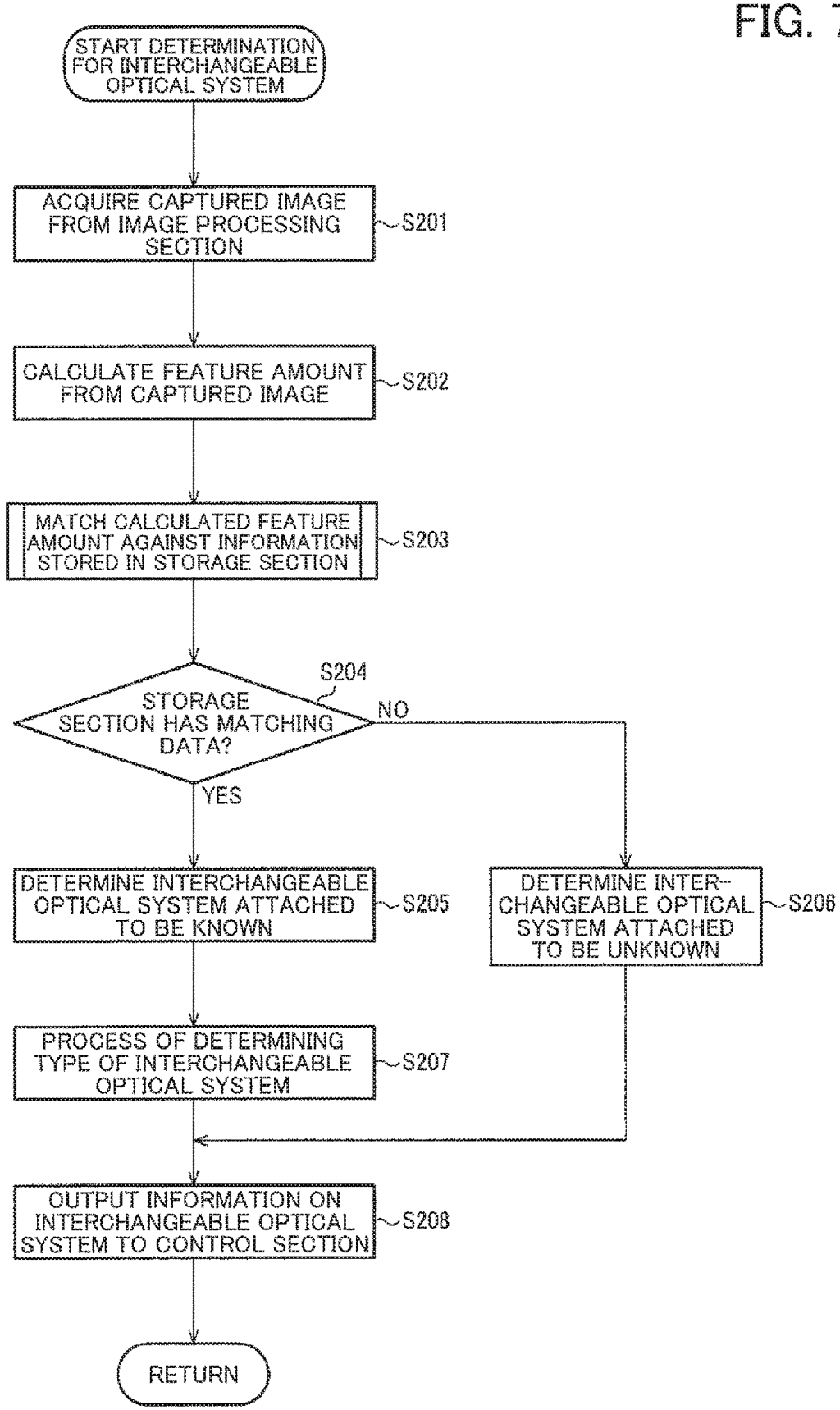
FIG. 7 is a flowchart illustrating a determination process of the interchangeable optical system.

FIG. 7 is a flowchart illustrating the process in S102. When this process starts, first of all, the interchangeable optical system determination section 340 acquires a captured image from the image processing section 310 (S201), and calculates a feature amount representing the size or the shape of an image circle or a luminance distribution on the captured image or any combination of these pieces of information (S202). The image circle is a substantially circular area representing a range on which light, for forming an image, is made incident after passing through the optical system (the interchangeable optical system 100 and the optical system 240 in this example). If the image circle is smaller than the image sensor 250, the captured image has a relatively bright area (with high luminance) inside the image circle and a relatively dark area (with low luminance) outside the image circle, as illustrated in FIG. 8.

Thus, a feature amount related to the image circle can be calculated from the captured image as follows for example. Specifically, the image is divided into small areas, and a direction of a histogram or edge, a change in the direction of an edge, or the like is obtained in each of the small area as a result of the division. The feature amount related to the image circle as used herein may be information representing characteristics of a part of the image circle (such as presence or absence of a notch, for example) or information representing the characteristics of the entire image circle (a size, for example). The feature amount of the entire or a part of the image circle on the image may be calculated using the feature amount calculated in each of small areas described above. Specifically, the feature amount of the image circle may be obtained by using the feature amount obtained from some of the plurality of areas. For example, a feature amount of an area determined to include a notch or the like may be used as the feature amount of the image circle. Alternatively, the feature amount of the image circle may be obtained from the feature amounts from all of the plurality of areas (an area corresponding to the entire captured image in a narrow sense). For example, information on an area at least including the entire image circle in the captured image is suitably used for obtaining the size of the like of the image circle. In a narrow sense, the feature amount of the image circle may be obtained based on the entire captured image. The feature amount of each of the small areas obtained by dividing the image and the feature amount of the entire or a part of the image circle on the image can be calculated through a known process. Note that a feature amount can be obtained from an image in various known ways, and thus a method other than that involving dividing the image into small areas may be employed.

The image circle varies among optical systems, and the calculated feature amount should differ among the interchangeable optical systems 100. Thus, the interchangeable optical system determination section 340 determines whether the interchangeable optical system 100 is a known or unknown optical system based on the feature amount. The optical system is determined to be known or unknown with a feature amount of the image circle calculated as described above matched against feature patterns of the image circles stored in the storage section 370.

Figures 8, 9:
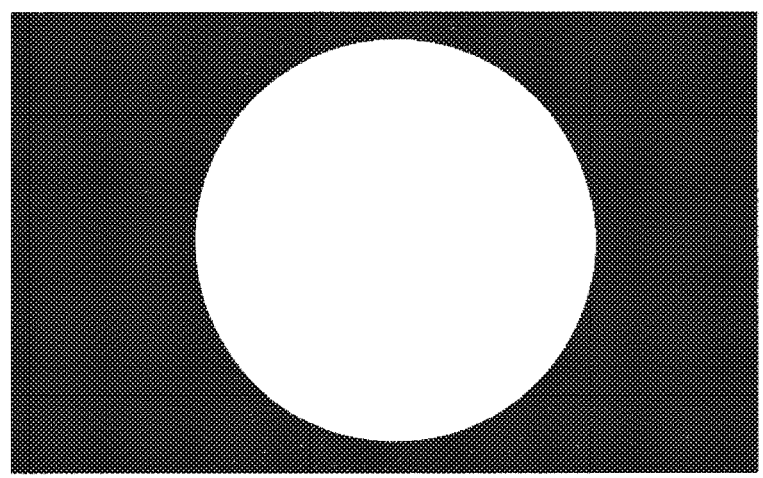
FIG. 8 is a diagram illustrating an example image circle in a captured image.
FIG. 9 is a table illustrating a configuration example of data used for a determination process of determining whether the interchangeable optical system is a known or unknown optical system.

For example, as illustrated in FIG. 9, the interchangeable optical system 100 may be designed in such a manner that an image with a notched image circle is obtained. This notch on the image may take various shapes, depending on how the interchangeable optical system 100 is designed. Thus, when an image has a notch, the interchangeable optical system is determined to be known or unknown with a feature amount representing a shape of an image circle calculated from the image matched against shapes of image circles stored in advance (S203). Specifically, as illustrated in FIG. 9, information associating a feature amount (data on a shape of an image circle in this example) with a result of determination that is a known or unknown optical system may be stored in the storage section 370 in advance, and a process of matching a feature amount obtained from the captured image with the feature amount in the information may be performed. FIG. 9 illustrates an example where the shape data is image data as a result of extracting a part of the captured image (data as a group of pixel values) for the sake of description. However, this should not be construed in a limiting sense, and a result of a certain conversion process on a pixel value may be stored as the feature amount (shape data). Thus, modifications employing various types of feature amounts may be made.

The determination result is obtained based on whether or not matching data has been found (S204). For example, the determination result "known" may be obtained when the feature amount obtained from the captured image matches a feature amount associated with known in FIG. 9 (when the image circle in the captured image has a notch) (S205). The determination result "unknown" may be obtained if the feature amount of a captured image, such as that illustrated in FIG. 10, does not match the feature amount in FIG. 9 (S206). Various known methods may be employed for the matching (matching process). A scaling process or a rotation process may be performed for the matching process.

Figures 10, 11, 12:
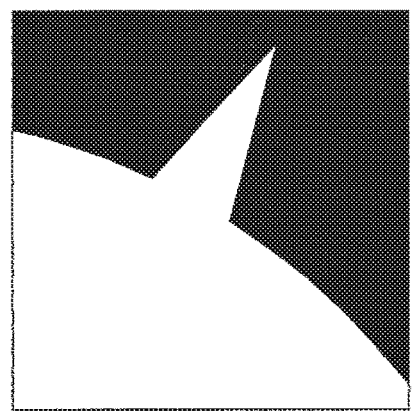
FIG. 10 is a diagram illustrating an example feature amount (shape data) determined to be an unknown optical system.
FIG. 11 is a table illustrating a configuration example of data used for an identification process of the type of the interchangeable optical system.
FIG. 12 is a table illustrating a configuration example of data used for determination of step amount information based on the type of the interchangeable optical system.

When the determination result is "known", the specific type of the interchangeable optical system 100 is identified (S207). The feature amount may be further used to identify the type. For example, as illustrated in FIG. 11, information (table data) associating the size of an image circle with the type may be stored in the storage section 370. In such a case, the type of the interchangeable optical system 100 is identified through a process of comparing information representing the size of the image circle, which is one calculated feature amount, with the table data in FIG. 11. For example, in the example illustrated in FIG. 11, when the feature amount indicates that the size of the image circle is 300, the type of the interchangeable optical system 100 can be identified as a type A.

The interchangeable optical system determination section 340 outputs information on the interchangeable optical system 100 to the control section 320 based on the determination result (S208). Specifically, information indicating that the interchangeable optical system 100 attached is known and information (optical characteristics information) on the type of the interchangeable optical system 100 attached are output to the control section 320 when the determination result is "known". On the other hand, information indicating that the interchangeable optical system 100 attached is unknown is output to the control section 320 when the determination result is "unknown".

Referring back to FIG. 6, the control section 320 determines whether to use the first step amount reference value determination section 350 or to use the second step amount reference value determination section 360 based on the result obtained in S102.

Specifically, whether the interchangeable optical system 100 is a known or unknown optical system is determined based on the information thus acquired (S103). If the information indicates "known", the information indicating the type of the interchangeable optical system 100 is transmitted to the first step amount reference value determination section 350, and the step amount reference value is obtained (S104).

The process in S104 may be performed as a process of referring to the table data stored in the storage section 370 for example. FIG. 12 illustrates an example of the table data. As illustrated in FIG. 12, the table data is information associating the type of an optical system with the step amount reference value X. Thus, when the type of the interchangeable optical system 100 has been identified in the process in S102 (S207 to be more precise), the step amount reference value associated with the identified type may be selected and output. As illustrated in FIG. 12, the step amount reference value may be set to be two values including one for AF and one for MF. Thus, the step amount information to be used by a single interchangeable optical system 100 can be different between the case where the AF operation is performed and the case where the MF operation is performed. The step amount information used for the AF operation is the wobbling amount or the like, and the step amount information used for the MF operation is the amount or the speed of the movement of the focus lens 220 relative to the user operation. With the step amount information thus being different between AF and for MF, appropriate focus control can be achieved with the step amount information settable to be different values. For example, in the example illustrated in FIG. 12, when the type of the interchangeable optical system 100 is identified to be the type A, a step amount reference value $X_{A\_af}$ is used in the AF mode and a step amount reference value $X_{A\_mf}$ is used in the MF mode.

When the determination result is "unknown", a start command is transmitted to the second step amount reference value determination section 360, and the step amount reference value is obtained (S105). As described above, the step amount reference value obtained in step S105 may be a given setting value including various setting values. This setting value may be set to be different between the AF mode and the MF mode.

The control section 320 transmits the step amount reference value to the step amount control section 211. The step amount control section 211 generates a control signal for the optical system 240, based on the obtained step amount reference value, and transmits the signal to the optical system control section 213 (S106). The step amount reference value may include two values including one for AF and one for MF as described above. Thus, the control signal output to the optical system control section 213 needs to be a signal corresponding to the current mode. For example, the first step amount reference value determination section 350 and the second step amount reference value determination section 360 may output only one of the two step amount reference values depending on which one of the AF mode or the MF mode is the current mode. Alternatively, the first step amount reference value determination section 350 and the second step amount reference value determination section 360 may output both of the two step amount reference values, and the control section 320 or the step amount control section 211 may select an appropriate one of the two values.

The optical system control section 213 applies current (voltage) to the optical system driving section 215, based on the control signal received, to drive the optical system 240. Thus, the focus control using an appropriate step amount information, depending on whether the interchangeable optical system 100 is a known or unknown optical system, can be implemented.

In the present embodiment described above, the processing section 300 obtains the feature amount representing at least one of the shape of the image circle, the size of the image circle, and the luminance distribution information based on the captured image, and performs a process of determining whether the interchangeable optical system 100 attached is a known or unknown optical system based on the feature amount.

In the process described above, the process of determining whether the attached optical system is a known or unknown optical system is performed by using the shape of the image circle as in FIG. 9 and FIG. 10. Alternatively, the size or the luminance distribution information may be used. The size of the image circle may be based on whether there is an area, such as a notch or protrusion portion described above for example, different from a substantially circular shape as a reference, or may be based on circularity (how close it is to a true circle). The size of the image circle may be represented by a radius or a diameter, a circumference length (perimeter), an area, or various other types of information representing the size. The luminance distribution information indicates a luminance in each area of the image circle. For example, even when an image of an achromatic and uniform subject is captured with the optical system, the brightness (luminance) is not necessarily entirely uniform in the image circle. In other words, one area may be darker than the other. In such a case, the position and the size in the image circle of the dark area depend on the characteristics of the interchangeable optical system 100. Thus, the determination process for the interchangeable optical system 100 can be performed with the luminance distribution information serving as the feature amount. The luminance distribution information may be a group of pieces of luminance information on pixels, a group of luminance values each corresponding to an area including a plurality of pixels, or a luminance of some of the pixels or the areas. Thus, various types of information representing the luminance characteristics of pixels of the captured image may be employed.

Thus, the process of determining whether the interchangeable optical system 100 is a known or unknown optical system can be performed based on the feature amount obtained from a captured image. As described above, the connection section 260 may have no electrical contact used for acquiring information representing the status of the interchangeable optical system 100. Without the electrical contact, a failure of the apparatus due to a sterilization process or a disinfection process can be prevented as described above. Thus, in the present embodiment, the information on the optical characteristics might not be acquirable from the interchangeable optical system 100 using a sensor such as a potentiometer as in JP-A-2005-250127. Still, the step amount information can be appropriately set with the feature amount obtained from the captured image used for determining whether the optical system is a known or unknown optical system.

The processing section 300 may perform the determination process of determining whether the interchangeable optical system 100 attached is a known or unknown optical system based on the feature amount, and perform an identification process of identifying the type of the interchangeable optical system 100 based on the feature amount if the interchangeable optical system 100 has been determined to be known.

Thus, not only the determination process of determining whether the optical system is a known or unknown optical system but also the identification process of identifying the type of the known optical system can be performed based on the feature amount obtained from the captured image. As described above, various types of information on the image circle can be used as the feature amount. Thus, different feature amounts can be used for the determination process and for the identification process. Shapes with and without a notch are largely different from each other. This ensures a highly accurate result of the process of determining whether the optical system is a known or unknown optical system using the feature amount based on the shape. The identification process is performed to identify the type only when the result of the determination process is "known". In other words, the identification process can be skipped if the result is "unknown", so that a process load can be reduced.

The processing section 300 performs the determination process based on the feature amount representing the shape of the image circle, and may perform the identification process based on the feature amount representing the size of the image circle. Specifically, the determination process may be performed through the matching process using the data illustrated in FIG. 9, and the identification process may be performed through the matching process using the data illustrated in FIG. 12.

Thus, the determination process and the identification process can be implemented with a combination of specific feature amounts related to the image circle. The determination process may be performed using a feature amount representing a feature other than the shape, and the identification process may be performed using a feature amount representing a feature other than the size. The combination of feature amounts used for the processes can be modified in various ways. The feature amount used for each process is not limited to a single feature amount. Thus, a modification of using a combination of two or more feature amounts for the determination process or using a combination of two or more feature amounts for the identification process may be employed.

The processing section 300 may perform the determination process of determining whether the interchangeable optical system 100 is a known or unknown optical system during a white balance adjustment mode. Specifically, as described above, the step amount control process start determination section 330 may output a control signal for starting a process related to the step amount (turn ON a start flag) during the white balance adjustment mode. Specifically, the feature amount representing at least one of the shape of the image circle, the size of the image circle, and the luminance distribution information is obtained based on the captured image acquired during the white balance adjustment mode, and the determination process of determining whether the interchangeable optical system 100 attached is a known or unknown optical system is performed based on the feature amount.

When the feature amount related to the image circle is calculated from the captured image, a risk of erroneous determination needs to be reduced. For example, if the subject has a portion with a circular shape and there is a dark area such as a shadow area around the periphery of the circular shape, the captured image is classified into a circular area that is relatively bright and the other area that is relatively dark. Thus, the circular area might be erroneously determined as the image circle. JP-A-2010-35131 discloses an example where a zoom lens is moved to prevent such erroneous determination due to luminance characteristics of the subject. Unfortunately, this requires a complex and time consuming process, and thus is inconvenient.

Endoscope apparatuses are used for surgery and diagnosis where an error might lead to a critical problem. Thus, the subject needs to be in an appropriate color to be monitored. Thus, it is a common practice to perform a white balance adjustment process before the surgery or the like starts. In the white balance adjustment mode, a white balance adjustment process is performed with an image of an achromatic and uniform subject captured, to ensure high accuracy. The step amount control process performed under the white balance adjustment mode ensures a lower risk of erroneously determining the luminance characteristics of the subject as the image circle. Thus, the zoom lens needs not to be moved for the determination as in JP-A-2010-35131. The interchangeable optical system 100 attached to the endoscope apparatus before a surgery or the like starts is less likely to be exchanged during the surgery. Thus, for example, the step amount control process may only be performed during the white balance adjustment mode. This ensures an efficient step amount control process.

Furthermore, this configuration may be modified in such a manner that the step amount control process is performed during the white balance adjustment mode, and is also performed at a timing that is not during the white balance adjustment mode, or in such a manner that the step amount control process is skipped during the white balance adjustment mode.

The focus control section 210 controls the focus lens 220 in any one of the MF mode and the AF mode. The processing section 300 may output a mode control signal for operating the focus control section 210 in the MF mode, when the interchangeable optical system 100 attached is determined to be an unknown optical system.

This configuration can disable the AF mode when the interchangeable optical system 100 is an unknown optical system. As described above, the optimum step amount information is difficult to set for the interchangeable optical system 100 that is an unknown optical system. Thus, an AF operation performed with a step amount of a given setting value might result in an unstable behavior of the focus lens 220 such as vibration, depending on the interchangeable optical system 100 attached. The MF operation, involving the movement of the focus lens based on the user operation, can at least prevent such an unstable behavior of the focus lens 220 unintended by the user. All things considered, stable (safe) focus control can be achieved with the AF disabled when the interchangeable optical system 100 is determined to be an unknown optical system.

2.3 Modifications

Modifications of the embodiments are described. The identification process of identifying the type is performed (S207) when the interchangeable optical system 100 is determined to be a known optical system in S205 in FIG. 7. The interchangeable optical system 100 attached according to the present embodiment include numerous types of optical systems. Thus, an unknown interchangeable optical system might have optical characteristics to be determined as a known optical system in the known/unknown determination process. For example, in the embodiment described above, an optical system with a notch of a given shape is determined to be a known optical system, and an optical system without such a feature is determined to be an unknown optical system. In this context, an unknown interchangeable optical system 100 with an image circle having a notch with a shape that is similar to the given shape might be attached.

In such a case, a result of the known/unknown determination process might be "known". This results in a failure to perform appropriate focus control due to the absence of step amount information (step amount reference value) suitable for such an interchangeable optical system 100, in the storage section 370.

Thus, the processing section 300 may determine that the interchangeable optical system 100 is an unknown optical system when the type of the interchangeable optical system 100, which has been determined to be a known optical system in the determination process, cannot be identified with the identification process.

Thus, an attached unknown interchangeable optical system 100 with optical characteristics resulting in an erroneous result (known) in the known/unknown determination process, can then be correctly determined to be an unknown optical system based on a result of the identification process. Thus, appropriate focus control can be achieved.

Figure 13:
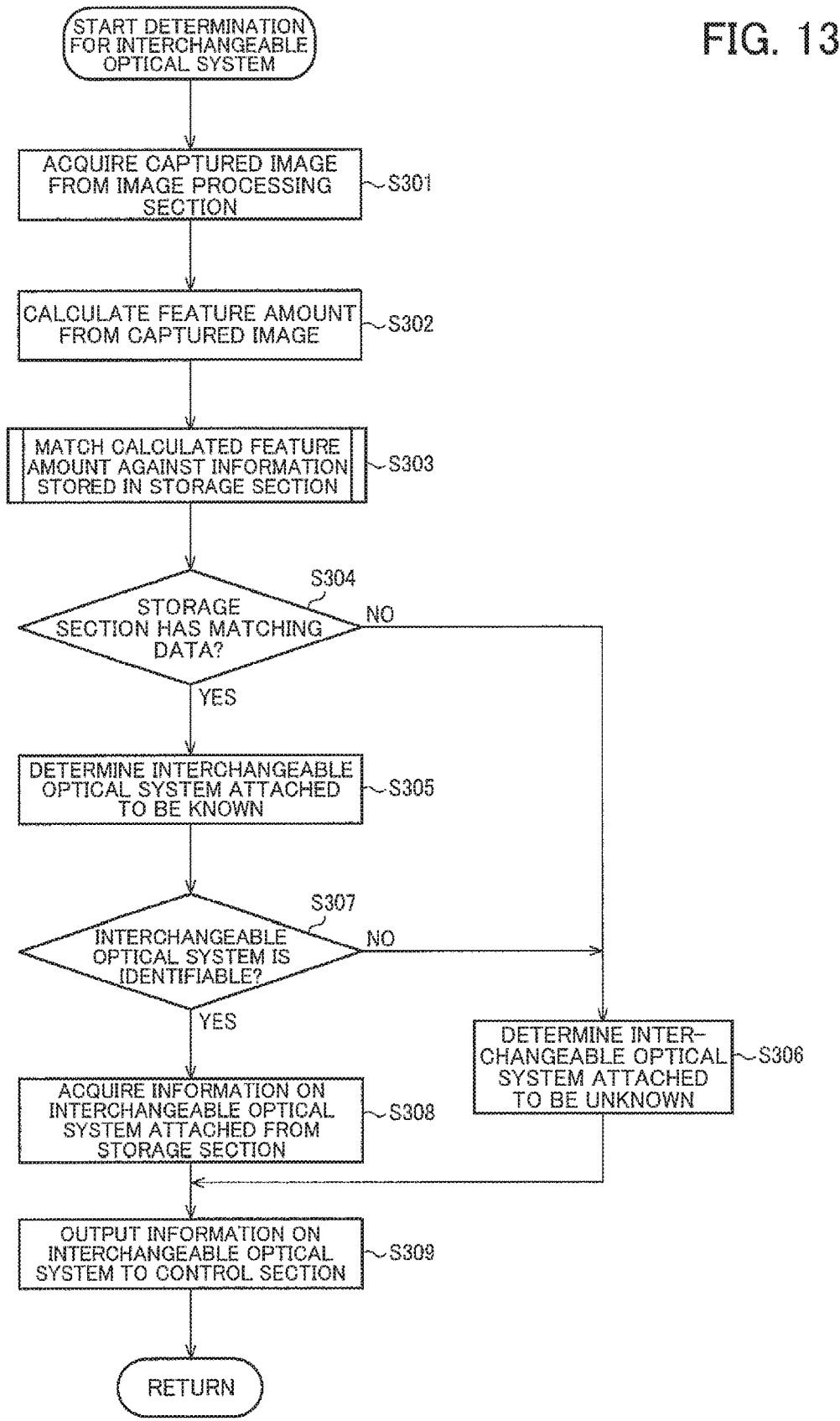
FIG. 13 is another flowchart illustrating a determination process for the interchangeable optical system.

FIG. 13 is a detailed flowchart. S301 to S306 in FIG. 13 are the same as S201 to S206 in FIG. 7. In FIG. 13, when the interchangeable optical system 100 is determined to be a known optical system in S305, whether or not the interchangeable optical system 100 is identifiable is determined (S307). This determination can be made by determining whether or not there is matching data in data, as illustrated in FIG. 11 or the like, in the storage section 370. For example, if a value of the feature amount (the size of the image circle) from the captured image is 500, none of the optical systems A, D, and E in the data in FIG. 11 match. If there is no matching data in the storage section 370 as described above, the optical system is determined to be unidentifiable, and the process proceeds to S306 to determine that the interchangeable optical system is an unknown optical system. On the other hand, when matching data is found, information on the interchangeable optical system 100 corresponding to the matching data is acquired (S308). The process in S309 is the same as in S208 in FIG. 7.

Figure 14:
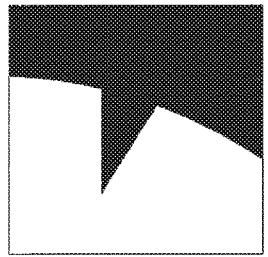
FIG. 14 is a table illustrating another configuration example of data used for an identification process of the type of the interchangeable optical system.

In the above-described embodiment, the two stage process is described including performing the known/unknown determination process and then performing the identification process when a result of the determination process is "known". However, the process performed by the interchangeable optical system determination section 340 is not limited to this. For example, data as illustrated in FIG. 14 may be stored in the storage section 370, and the matching process may be performed using the data. In this example, the storage section 370 stores information associating each type of the image circle with a feature amount with which the type can be identified. Specifically, the type of the interchangeable optical system 100 is associated with the shape and the size of the image circle.

The interchangeable optical system determination section 340 performs matching to determine whether or not the feature amount obtained from the captured image matches any of the patterns as in S204 in FIG. 7. The determination result is "known" when a matching pattern is found, and is "unknown" when no matching pattern is found, as in FIG. 7. In the example illustrated in FIG. 14, when the matching pattern is found, the type of the interchangeable optical system 100 is also identified. In other words, the interchangeable optical system 100 determined to be a known optical system can have the type determined at the timing of the determination. This configuration is free of a situation where the type of the optical system determined to be known cannot be identified as in the modification described above.

Thus, in this modification, the processing section 300 performs a process of comparing a feature amount with first to N-th (N being an integer equal to or larger than 2) feature amounts respectively corresponding to first to N-th known interchangeable optical systems. When the feature amount is determined to match an i-th (i being an integer satisfying 1≤i≤N) feature amount, the interchangeable optical system 100 attached is determined to be a known optical system, and the type of the interchangeable optical system 100 attached is determined to be the same as a type of an i-th interchangeable optical system. When the feature amount is determined not to match any of the first to the N-th feature amounts, the interchangeable optical system 100 attached is determined to be an unknown optical system.

Thus, the known/unknown determination process and the type identification process can be collectively executed. As described above, the process performed by the interchangeable optical system determination section 340 can be modified in various ways.

3. Second Embodiment

A second embodiment is described below. When an optical system includes a zoom lens, the size of the image circle and like vary depending on the position of the zoom lens (zoom ratio). Thus, the zoom lens position needs to be taken into consideration for the process using the feature amount related to the image circle.

Figure 15:
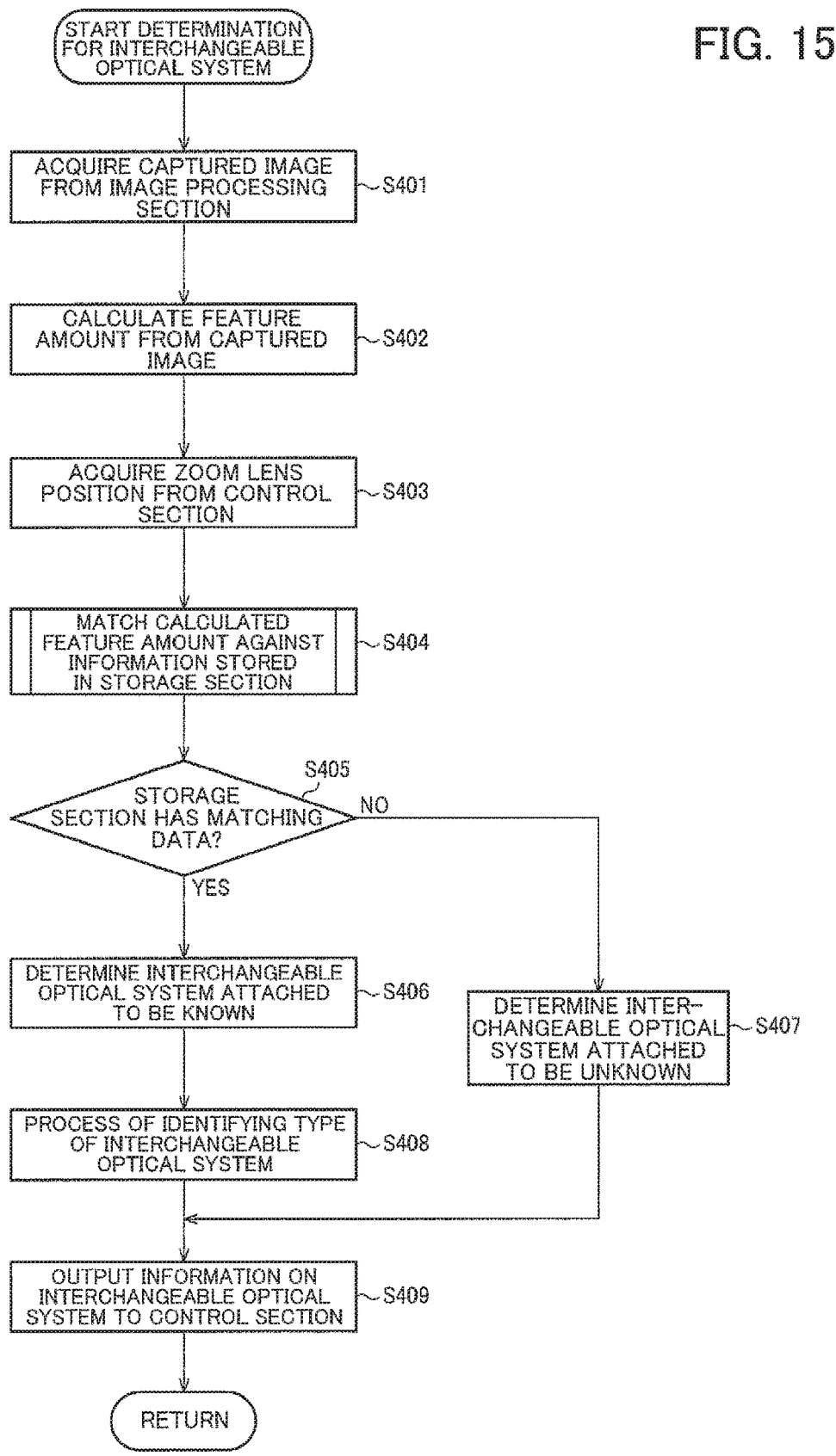
FIG. 15 is another flowchart illustrating a determination process for the interchangeable optical system.

FIG. 15 is a flowchart illustrating a step amount control process according to the present embodiment. S401 and S402 are the same as S201 and S202 in FIG. 7. In the present embodiment, the zoom lens position is acquired from the control section 320 (S403).

Then, for the matching against the data stored in the storage section 370, both of the zoom lens position and the feature amount obtained from the captured image are used (S404). For example, the storage section 370 may store data similar to that in FIG. 9, and the matching process may be performed with at least one of the stored data and the feature amount corrected (normalized) based on information on the zoom lens position. For example, the storage section 370 stores the shape information on the image circle obtained with the zoom lens position at a given reference position, and a scaling process is performed on the shape information in accordance with the zoom lens position. Then, the resultant information is compared with the feature amount. When the zoom lens position is different from the reference position, the shape information changes from that obtained with the reference position due to a change in the size of the image circle. Thus, the correction using the information on the zoom lens position may be performed so that highly accurate process can be performed with the difference offset. Alternatively, a correction process (normalization process) corresponding to the zoom lens position may be performed on the feature amount obtained from the captured image.

The known/unknown determination process (S405 to S407) based on the determination result is the same as that in S204 to S206 in FIG. 7. Both the feature amount obtained from the captured image and the zoom lens position are also used in the type identification process (S408). For example, the storage section 370 stores table data associating the type of the interchangeable optical system 100, the feature amount of the image circle, and the zoom lens position with each other as illustrated in FIG. 16. In this state, the feature amount obtained in S402 and the zoom lens position acquired in S403 are both used for matching against the table data in FIG. 16, to search for a matching data.

The shape of the graphs illustrated in FIG. 1A and FIG. 1B changes in accordance with the zoom lens position. Thus, different types of step amount information need to be used for the focus control for a single optical system, in accordance with the zoom lens position.

In view of this, the storage section 370 stores table data illustrated in FIG. 17. FIG. 17 illustrates information associating the type of the interchangeable optical system 100, the zoom lens position, and the step amount reference values (two values for AF and for MF). The first step amount reference value determination section 350 uses both the type of the interchangeable optical system 100 identified in S408 and the zoom lens position acquired in S403, to perform matching against the data in FIG. 17, and outputs a matching step amount reference value (S104 in FIG. 6). The second step amount reference value determination section 360 may output a step amount reference value that varies depending on the zoom lens position, instead of using the same setting value every time (S105 in FIG. 6). The zoom lens position may change during monitoring (during surgery in a narrow sense). An appropriate step amount reference value might change when the zoom lens position changes. Thus, a modification may be employed in which the process of determining the step amount reference value by referring to the table data in FIG. 17 or the like is performed each time the change in the zoom lens position is detected, or the process is performed once in every predetermined period of time. During a single series of surgeries, the type of the interchangeable optical system 100 is less likely to change, and thus the known/unknown determination process or the type identification process may be skipped.

In the present embodiment described above, the optical system 240 includes the zoom lens 230 for adjusting a focal length. The processing section 300 obtains a feature amount representing at least one of the shape of the image circle, the size of the image circle, and the luminance distribution information based on the captured image, and performs the determination process of determining whether the interchangeable optical system 100 attached is a known or unknown optical system, based on the feature amount thus obtained and the position of the zoom lens.

The known/unknown determination process can be accurately performed in accordance with the zoom lens position of the optical system 240. The method of normalizing the feature amount based on the zoom lens position is described with reference to FIG. 9. Alternatively, the determination process may be performed by referring to table data, with a section (item, element) for information on the zoom lens position, as in FIG. 16.

The processing section 300 may identify the type of the interchangeable optical system 100 when the interchangeable optical system 100 attached is determined to be a known optical system, and perform the first step amount determination process of determining the step amount information based on the type of the interchangeable optical system 100 thus identified and the position of the zoom lens.

With this configuration, the determination process for the step amount information can be performed in accordance with the zoom lens position of the optical system 240, whereby appropriate step amount information can be determined. FIG. 16 illustrates an example of identifying the type by referring to the table data with a section for the information on the zoom lens position. Alternatively, the type identification process may be performed by normalizing the feature amount based on the zoom lens position. Thus, the zoom lens position may be in one section of the table data or may be used for the normalization process for any of the determination process, the identification process (S404 and S408 in FIG. 15), and the step amount information determination process (S104 and S105 in FIG. 6) for the interchangeable optical system 100. When the normalization process is performed, the feature amount is normalized in S404 and S408, and the step amount reference value to be obtained is normalized in S104 and S105.

Figure 18:
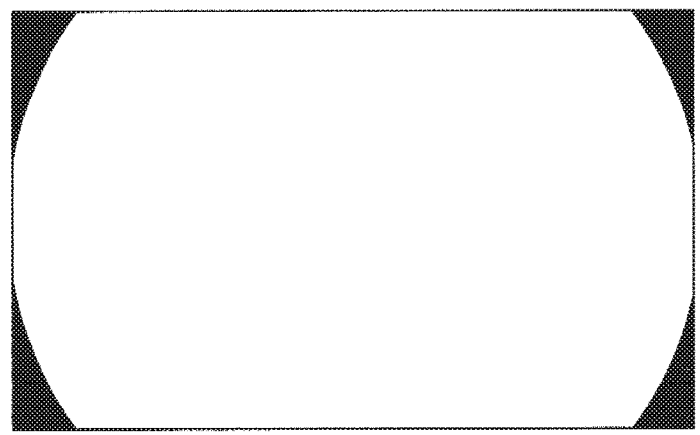
FIG. 18 is a diagram illustrating an example captured image in a case where the image circle has a larger size than the size of the image sensor.

When the image circle is larger than the image sensor 250, the image circle might have a part outside the captured image as illustrated in FIG. 18A. If such an outside part has a notch or a protrusion, information on such a feature is lost and information on the luminance distribution cannot be acquired for such an area. When the image sensor 250 is entirely included in the image circle, the size of the image circle is difficult to estimate from the captured image.

Thus, when the zoom lens 230 is provided, the zoom lens position may be adjusted to achieve a smallest possible image circle size. Thus, the control section 320 may output an instruction to move the zoom lens 230 toward the wide angle end to the optical system driving section 215 so that the entire image circle is included in the image, and then obtain the feature amount by using the captured image.

More specifically, the processing section 300 outputs instruction information to the focus control section 210 to move the position of the zoom lens 230 toward the wide angle end, when executing the determination process for the interchangeable optical system 100.

Thus, a larger area of the image circle is more likely to be in the captured image as illustrated in FIG. 8, so that the feature amount can be appropriately calculated.

In the present embodiment, an example is described where the two step process including the known/unknown determination process and the type identification process is performed as illustrated in the flowchart in FIG. 15. Alternatively, a modification where these processes can be collectively performed by determining whether or not there is matching data can be employed as in the modification of the first embodiment (FIG. 14).

4. Third Embodiment

A third embodiment is described below. An endoscope apparatus according to the present embodiment includes an operation section (operation interface) 270 receiving a user input operation as illustrated in FIG. 2. This operation section 270 may be a button that can be pressed, a dial that can be rotated, or a stick-like member that can be pivoted. Furthermore, the operation section 270 may be a touch panel or the like. Thus, the specific configuration of the operation section 270 can be modified in various ways.

Figure 19:
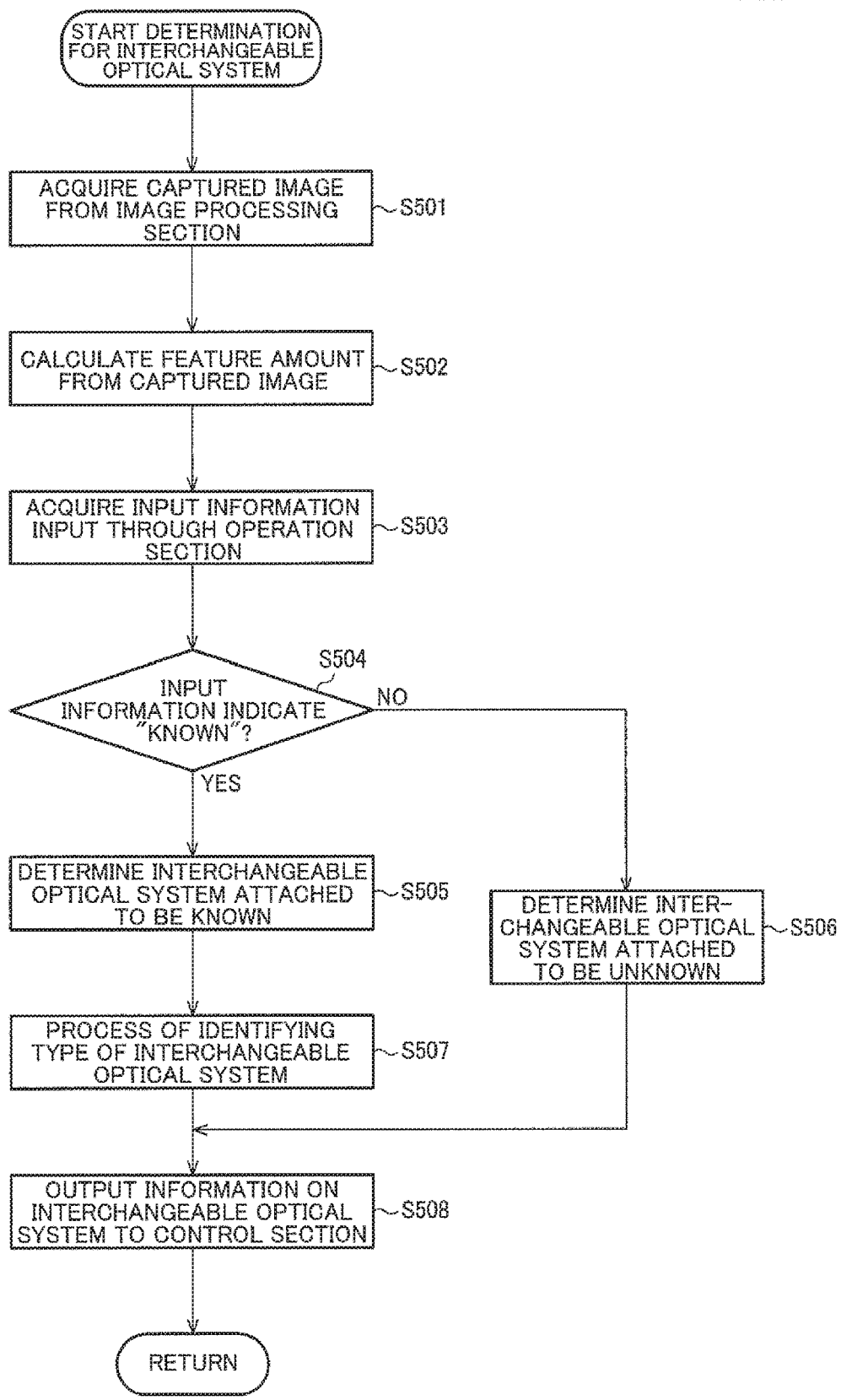
FIG. 19 is another flowchart illustrating a determination process for the interchangeable optical system.

FIG. 19 is a flowchart illustrating a process according to the present embodiment. S501 and 502 in FIG. 19 are the same as S201 and S202 in FIG. 7. In the present embodiment, the processing section 300 (control section 320) acquires input information from the operation section 270 (S503). Note that S503 is not limited to the acquisition at the timing illustrated in FIG. 19, and other acquisition timing such as that before the step amount control process may be employed for example.

The input information in this example indicates whether the interchangeable optical system 100 attached is a known or unknown optical system. The interchangeable optical system 100 is expected to be manually attached to the connection section 260 by the user. Thus, the user (a physician, a scopist) who operates the endoscope apparatus is aware of the type of the interchangeable optical system 100 attached. For example, the user can determine whether or not the interchangeable optical system 100 is "known" to the endoscope apparatus, based on information indicating that the user has been using the optical system or on information indicating that the optical system is an accessory product manufactured by the manufacturer of the endoscope apparatus. Furthermore, the user can determine that the interchangeable optical system 100 is "unknown" to the endoscope apparatus, based on information indicating the optical system is a new product or is manufactured by a third party. In S503, the user inputs this information indicating known or unknown on the operation section 270 as input information. A modification where a display image instructing the input is displayed before S503 may be employed.

The interchangeable optical system determination section 340 performs the known/unknown determination process based on the input information (S504). In the present embodiment, when the input information indicates that the optical system is known, the optical system may be determined to be known (S505). When the input information indicates that the optical system is unknown, the optical system may be determined to be unknown (S506). Alternatively, known may be set as default setting for achieving higher usability. In such a case, the optical system may be determined to be known if there is no user input, and may be determined to be unknown if there is a user input. Thus, the user is requested to perform input on the operation section 270, only when an unknown interchangeable optical system 100 is used.

A process after the known/unknown determination process based on the input information (S507, S508) is the same as that in S207 and S208 in FIG. 7. Specifically, the type identification process may be performed by referring to data (data illustrated in FIG. 11 for example) stored in the storage section 370 if the optical system is "known", and the step amount reference value may be determined based on the type. The step amount reference value may be set to be the given setting value if the optical system is "unknown". Alternatively, when the optical system 240 includes the zoom lens 230, the process may be performed using both the feature amount and the zoom lens position as in the example described in the second embodiment with reference to FIG. 15 to FIG. 17.

In the present embodiment described above, the operation section 270 that receives the input information input by the user is provided. The processing section 300 performs the determination process based on the input information received by the operation section 270.

Thus, the known/unknown determination process is performed based on the input information from the user, and thus can be accurately performed.

The operation section 270 may receive the input information, indicating whether the interchangeable optical system 100 attached is a known or unknown optical system, and the identification process of identifying the type of the interchangeable optical system 100 may be performed based on the feature amount, when the interchangeable optical system 100 attached is determined to be a known optical system based on the input information.

With this configuration, the endoscope apparatus is in charge of the type identification process and a process of determining specific step amount information (step amount reference value) based on the feature amount, so that an excessively large operation load would not be imposed on the user.

With a relatively larger operation load is required for the user, not only the information indicating "known" or "unknown" but also information for identifying the type may be input as the input information. Specifically, the user is requested to input the information on the type of the interchangeable optical system 100 attached.

Thus, the operation section 270 receives first input information for identifying the type of the interchangeable optical system 100 attached or second input information indicating that the interchangeable optical system 100 is "unknown", as the input information. Then, the processing section 300 may determine the step amount information based on the first step amount determination process when the first input information is input, and may determine the step amount information based on the second step amount determination process when the second input information is input.

Thus, not only known/unknown determination but also the identification process for the known optical system may be performed based on the input information. Thus, the determination process and the identification process can be accurately performed.

Although the three embodiments that are the first to the third embodiments to which the invention is applied and the modifications thereof have been described in detail above, the invention is not limited to the first to the third embodiments and the modifications thereof, and various modifications and variations may be made without departing from the scope of the invention. The plurality of elements disclosed in the first to the third embodiments and the modifications may be combined as appropriate to implement the invention in various ways. For example, some of all the elements described in the first to the third embodiments and the modifications may be deleted. Furthermore, elements in different embodiments and modifications may be combined as appropriate. Any term cited with a different term having a broader meaning or the same meaning at least once in the specification and the drawings can be replaced by the different term in any place in the specification and the drawings. Thus, various modification and application can be made without departing from the gist of the present invention.

What is claimed is:

1. An endoscope apparatus comprising:
   an optical system including a focus lens configured to adjust an in-focus object position;
   a connector to which an interchangeable optical system is connected;
   an image sensor configured to output a captured image based on the optical system and the interchangeable optical system; and
   a processor including hardware, the processor being configured to:
      determine whether the interchangeable optical system is a known or is an unknown optical system,
      determine step amount information, indicating a control amount of the focus lens of the optical system, based on a first step amount determination when the interchangeable optical system is determined to be a known optical system, or based on a second step amount determination, different from the first step amount determination, when the interchangeable optical system is determined to be an unknown optical system,
      control the focus lens based on the determined step amount information, and
      obtain a feature amount representing at least one of a shape of an image circle, a size of the image circle, and luminance distribution information based on the captured image, wherein the determining of whether the interchangeable optical system attached is a known or is an unknown optical system is based on the obtained feature amount.

2. The endoscope apparatus as defined in claim 1, wherein the processor determines whether the interchangeable optical system attached is a known or is an unknown optical system is based on the feature amount, and identifies a type of the interchangeable optical system based on the feature amount when the interchangeable optical system is determined to be a known optical system.

3. The endoscope apparatus as defined in claim 2, wherein the processor determines whether the interchangeable optical system attached is a known or is an unknown optical system is based on the feature amount representing the shape of the image circle, and the identifying is based on the feature amount representing the size of the image circle.

4. The endoscope apparatus as defined in claim 2, wherein the processor determines that the interchangeable optical system that has been determined to be a known optical system is an unknown optical system when the type of the interchangeable optical system is unidentifiable.

5. The endoscope apparatus as defined in claim 2, wherein the processor, when the interchangeable optical system attached is determined to be a known optical system, first step amount determination determines the step amount information based on the type of the interchangeable optical system identified.

6. The endoscope apparatus as defined in claim 1, wherein:
   the processor performs a comparison process of comparing the feature amount with first to N-th feature amounts respectively corresponding to first to N-th known interchangeable optical systems, N being an integer equal to or larger than 2, and
   when the feature amount is determined to match an i-th feature amount, the processor determines that the interchangeable optical system attached is a known optical system and identifying the type of the interchangeable optical system attached to be same as a type of an i-th interchangeable optical system, i being an integer satisfying 1≤i≤N, and
   when the feature amount is determined not to match any of the first to the N-th feature amounts, the processor determines that the interchangeable optical system attached to be an unknown optical system.

7. The endoscope apparatus as defined in claim 1, wherein:
   the optical system including a zoom lens for adjusting a focal length,
   the processor determines whether the interchangeable optical system attached is a known or unknown optical system based on the feature amount determined and a position of the zoom lens.

8. The endoscope apparatus as defined in claim 7, wherein the processor identifies a type of the interchangeable optical system when the interchangeable optical system attached is determined to be a known optical system, and first step amount determination determines the step amount information based on the type of the interchangeable optical system identified and the position of the zoom lens.

9. The endoscope apparatus as defined in claim 1, wherein the processor performs the second step amount determination of setting the step amount information to be a given setting value when the interchangeable optical system attached is determined to be an unknown optical system.

10. The endoscope apparatus as defined in claim 1, wherein the connector being a connector having no electrical contact used for acquiring information representing a status of the interchangeable optical system.

11. The endoscope apparatus as defined in claim 1, wherein the processor:
controls the focus lens in any one of a ManualFocus mode and an AutoFocus mode, and
controls the focus lens in the ManualFocus mode when the interchangeable optical system attached is determined to be an unknown optical system.

12. An endoscope apparatus comprising:
an optical system including a focus lens configured to adjust an in-focus object position;
a connector to which an interchangeable optical system is connected;
an image sensor configured to output a captured image based on the optical system and the interchangeable optical system;
an operation interface for receiving input information input by a user; and
a processor including hardware, the processor being configured to:
  determine whether the interchangeable optical system is a known or is an unknown optical system,
  determine step amount information, indicating a control amount of the focus lens of the optical system, based on a first step amount determination when the interchangeable optical system is determined to be a known optical system, or based on a second step amount determination, different from the first step amount determination, when the interchangeable optical system is determined to be an unknown optical system,
  controlling the focus lens based on the determined step amount information,
  obtain a feature amount representing at least one of a shape of an image circle, a size of the image circle, and luminance distribution information based on the captured image,
  receive the input information indicating whether the interchangeable optical system attached is a known or is an unknown optical system, and
  identify a type of the interchangeable optical system based on the feature amount when the interchangeable optical system attached is determined to be a known optical system based on the input information.

13. The endoscope apparatus as defined in claim 12, wherein
the operation interface receiving, as the input information, first input information for identifying a type of the interchangeable optical system attached or second input information indicating that the interchangeable optical system is an unknown optical system,
the processor determines the step amount information based on the first step amount determination when the first input information is input, and determines the step amount information based on the second step amount determination when the second input information is input.

14. The endoscope apparatus as defined in claim 12, wherein the processor obtains the feature amount based on the captured image acquired during the white balance adjustment mode, and determines whether the interchangeable optical system attached is a known or is an unknown optical system based on the feature amount.

15. An endoscope apparatus comprising:
an optical system including a focus lens configured to adjust an in-focus object position and a zoom lens for adjusting a focal length;
a connector to which an interchangeable optical system is connected;
an image sensor configured to output a captured image based on the optical system and the interchangeable optical system; and
a processor including hardware, the processor being configured to:
  determine whether the interchangeable optical system is a known or is an unknown optical system,
  determine step amount information, indicating a control amount of the focus lens of the optical system, based on a first step amount determination when the interchangeable optical system is determined to be a known optical system, or based on a second step amount determination, different from the first step amount determination, when the interchangeable optical system is determined to be an unknown optical system,
  control the focus lens based on the determined step amount information, and
  move a position of the zoom lens toward a wide angle end, when performing the determination of whether the interchangeable optical system is a known or is an unknown optical system.

16. A method for operating an endoscope apparatus including an optical system including a focus lens configured to adjust an in-focus object position and a connector to which an interchangeable optical system is connected, the method comprising:
obtaining a feature amount representing at least one of a shape of an image circle, a size of the image circle, and luminance distribution information based on a captured image;
determining whether the interchangeable optical system is a known or is an unknown optical system based on the feature amount;
determining step amount information, indicating a control amount of the focus lens of the optical system, based on a first step amount determination when the interchangeable optical system is determined to be a known optical system or based on a second step amount determination, different from the first step amount determination, when the interchangeable optical system is determined to be an unknown optical system; and
controlling the focus lens based on the determined step amount information.

17. A method for operating an endoscope apparatus including an optical system including a focus lens configured to adjust an in-focus object position, a connector to which an interchangeable optical system is connected and an operation interface for receiving input information input by a user, the method comprising:
receiving input information indicating whether the interchangeable optical system attached is a known or unknown optical system;
determining whether the interchangeable optical system is a known or is an unknown optical system based on the input information;
determining step amount information, indicating a control amount of the focus lens of the optical system, based on a first step amount determination when the interchangeable optical system is determined to be a known optical system or based on a second step amount determination, different from the first step amount determination, when the interchangeable optical system is determined to be an unknown optical system;

controlling the focus lens based on the determined step amount information;

obtaining a feature amount representing at least one of a shape of an image circle, a size of the image circle, and luminance distribution information based on the captured image; and identifying a type of the interchangeable optical system based on the feature amount when the interchangeable optical system attached is determined to be a known optical system based on the input information.

18. A method for operating an endoscope apparatus including an optical system including a focus lens configured to adjust an in-focus object position and a zoom lens for adjusting a focal length, and a connector to which an interchangeable optical system is connected, the method comprising:

determining whether the interchangeable optical system is a known or is an unknown optical system;

determining step amount information, indicating a control amount of the focus lens of the optical system, based on a first step amount determination when the interchangeable optical system is determined to be a known optical system or based on a second step amount determination, different from the first step amount determination process, when the interchangeable optical system is determined to be an unknown optical system;

controlling the focus lens based on the determined step amount information; and moving a position of the zoom lens toward a wide angle end during the determining of whether the interchangeable optical system is a known or is an unknown optical system.

* * * * *